US010835682B2

(12) United States Patent
Senior et al.

(10) Patent No.: US 10,835,682 B2
(45) Date of Patent: Nov. 17, 2020

(54) DRIVE MECHANISM FOR AN INJECTION DEVICE

(71) Applicant: SANOFI-AVENTIS DEUTSCHLAND GMBH, Frankfurt am Main (DE)

(72) Inventors: James Alexander Senior, Warwick (GB); Elliot Baxter, Warwick (GB); David Aubrey Plumptre, Warwick (GB); Robert Frederick Veasey, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 227 days.

(21) Appl. No.: 16/061,617

(22) PCT Filed: Dec. 5, 2016

(86) PCT No.: PCT/EP2016/079696
§ 371 (c)(1),
(2) Date: Jun. 12, 2018

(65) Prior Publication Data
US 2019/0151557 A1 May 23, 2019

(30) Foreign Application Priority Data
Dec. 14, 2015 (EP) .................................. 15199710

(51) Int. Cl.
*A61M 5/31* (2006.01)
*A61M 5/315* (2006.01)
*A61M 5/145* (2006.01)

(52) U.S. Cl.
CPC .... *A61M 5/31536* (2013.01); *A61M 5/31541* (2013.01); *A61M 5/31583* (2013.01);
(Continued)

(58) Field of Classification Search
CPC .......... A61M 5/31536; A61M 5/31541; A61M 5/31585; A61M 5/31583;
(Continued)

(56) References Cited

U.S. PATENT DOCUMENTS

2015/0224266 A1    8/2015 Plumptre et al.

FOREIGN PATENT DOCUMENTS

WO    WO 2010/063687    6/2010
WO    WO 2011/060785    5/2011
(Continued)

OTHER PUBLICATIONS

International Search Report and Written Opinion in International Application No. PCT/EP2016/079696, dated Jun. 19, 2018, 6 pages.
(Continued)

*Primary Examiner* — Amber R Stiles
(74) *Attorney, Agent, or Firm* — Fish & Richardson P.C.

(57) ABSTRACT

The present disclosure relates to a drive mechanism for an injection device. The mechanism includes an inner body fixable inside a housing of the injection device and including an elongated shaft extending in an axial direction. The shaft includes an outer thread and a blocking structure on an outer circumference. A tubular-shaped display member has an inner thread engaged with the outer thread of the inner body. A dose member is axially displaceable relative to the inner body or the display member between a dose setting position and a dose dispensing position. A blocking ring is axially engageable with the dose member, rotationally fixed to the display member and includes a blocking element to axially engage with the blocking structure for blocking an axial displacement of the dose member from the dose setting position towards the dose dispensing position.

20 Claims, 10 Drawing Sheets

(52) U.S. Cl.
CPC ............... *A61M 5/31585* (2013.01); *A61M 2005/14506* (2013.01); *A61M 2005/3126* (2013.01); *A61M 2205/581* (2013.01); *A61M 2205/582* (2013.01)

(58) Field of Classification Search
CPC .. A61M 2005/14506; A61M 2205/582; A61M 2205/581; A61M 2005/3126; A61M 5/31528; A61M 5/31551; A61M 5/31511
See application file for complete search history.

(56) References Cited

FOREIGN PATENT DOCUMENTS

| | | | |
|---|---|---|---|
| WO | WO-2011060785 A1 * | 5/2011 | ........ A61M 5/31585 |
| WO | WO 2013/058697 | 4/2013 | |
| WO | WO 2013/170392 | 11/2013 | |

OTHER PUBLICATIONS

International Preliminary Report on Patentability in International Application No. PCT/EP2016/079696, dated Feb. 27, 2017, 8 pages.

* cited by examiner

DRIVE MECHANISM FOR AN INJECTION DEVICE

The present invention relates in one aspect to a drive mechanism for an injection device, such as a pen-type injector for setting and dispensing of a dose of a medicament. In particular, the invention relates to an injection device providing a minimum dose mechanism, i.e. a dose setting and dispensing mechanism that is only operable to dispense a dose if the dose exceeds a predefined minimum threshold.

BACKGROUND AND PRIOR ART

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, the dose setting as well as the dose dispensing procedure must be easy to operate and has to be unambiguous.

Typically, such devices comprise a housing including a cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast, injection devices of disposable type are to be discarded when the medicament in the cartridge has been dispensed or used-up.

Documents WO 2014/033197 A1 and WO 2014/033195 A1 disclose disposable and reusable drug delivery devices for selecting and dispensing a number of user variable doses of a medicament. These devices comprise a housing, a cartridge holder for retaining a cartridge containing the medicament, a piston rod displaceable relative to the cartridge holder, a driver coupled to the piston rod, a display member indicating a set dose and being coupled to a housing and to the driver, and a button coupled to the display member and to the driver.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential pre-fixed doses of a medication may be required. For example the range of doses may be needed to satisfy the therapeutic needs of different user groups, or to allow individual users to deliver a different dose at different times of the day e.g. in the morning or in the evening.

OBJECTS OF THE INVENTION

It is therefore an object of the present invention to provide a drive mechanism for an injection device that provides a minimum dose function. It is a further object that the drive mechanism also provides a maximum dose function. It is a further aim to provide a drive mechanism that allows for priming of the device, so that a user is able to dial and to deliver a rather small volume of medication, typically 2 international units (IU), to check whether flow occurs correctly through a needle assembly, that is releasably attachable to a distal dispensing end of the device.

Implementation of the desired minimum and/or maximum dose function should be achievable by modifying only a limited number of existing device components. It is a further aim to individually modify minimum and maximum dose values or dose sizes by changing only a single or only a few components of the device. Hence, the minimum and/or maximum dose function of the device or its drive mechanism should be configurable by interchanging only one or a few components of the device or its drive mechanism. It is a further aim, that the improved drive mechanism is universally applicable to a large variety of drive mechanisms and injection devices. In particular, the improved drive mechanism should be equally applicable to disposable injection devices as well as to reusable injection devices. Furthermore, and in one embodiment, the drive mechanism should be operable as a so-called fixed dose mechanism exclusively operable to set and to dispense a single or multiple doses of a pre-defined, hence 'fixed' size.

SUMMARY OF THE INVENTION

In a first aspect the invention relates to a drive mechanism for an injection device. The injection device is operable to set and to dispense multiple doses of variable size of a medicament, typically by way of injection. The drive mechanism of the injection device comprises the mechanically inter engaging components that are required to exert distally directed thrust to a piston of a cartridge filled with the liquid medicament. The drive mechanism comprises an inner body that is fixable inside a housing of the injection device. The inner body at least comprises an elongated shaft that extends in an axial direction (z) and having an outer thread. The outer thread is a helical thread and comprises a constant or varying pitch in the axial direction. The inner body is fixable inside the housing in a non-movable way. Hence, the inner body is axially as well as rotationally fixable inside a tubular or cylindrically-shaped housing of the injection device. The inner body and the housing may also be integrally formed. Hence, the inner body may be a portion of the housing.

The drive mechanism further comprises a tubular-shaped display member having an inner thread engaged or mating with the outer thread of the inner body. The tubular-shaped display member is axially displaceable relative to the inner body, in particular relative to its elongated shaft when rotating in a helical way. Typically, the pitch and friction of the threaded engagement of the display member and the inner body is such that the display member starts to rotate when it is subject to an axial force effect relative to the inner body.

In addition, the drive mechanism comprises a dose member that is axially displaceable between a dose setting position (S) and a dose dispensing position (D) relative to at least one of the inner body and the display member. It is axially displaceable relative to the inner body and/or to the display member. Typically, the dose member is rotatable along a helical path relative to the inner body for setting or dialing of a dose. Moreover, the dose member may be axially displaceable in a non-rotative but purely axial sliding manner relative to the inner body for dispensing of a dose. The dose member and the display member may be selectively rotationally engaged, typically by means of a clutch by way of which the rotational engagement between dose member and display member is either locked or released.

In a dose setting mode the clutch is typically closed, so that a torque applied to the dose member is transferred to the display member, which upon its threaded engagement with the inner body is then displaced axially relative to the inner body in unison with the dose member. For dose dispensing the clutch between display member and dose member may be released or opened so that the display member is allowed to rotate when returning into its initial position while the dose member is subject to a purely translational displacement. Hence, during dose dispensing the dose member may be rotationally locked to the inner body while the display member is free to rotate relative to the display body and hence relative to the dose member.

Depending on the specific embodiment of the drive mechanism either the rotating display member or the translationally displacing dose member is operably engaged with the piston rod for driving the piston rod in a distal dose dispensing direction during dose dispensing for displacing the piston of the cartridge in the distal direction.

The dose member and the display member are also axially engaged. When in the dose dispensing position or in the dose dispensing mode, hence when the clutch is disengaged a distally directed displacement of the dose member is transferred to a correspondingly distally directed displacement of the display member. Due to the permanent threaded engagement with the inner body, the display member also rotates and is displaced along a helical path during dose dispensing.

The drive mechanism further comprises a blocking ring that is axially engageable with the dose member and which is rotationally fixed to the display member. The blocking ring may be freely rotatable relative to the dose member. The blocking ring is permanently rotationally fixed to the display member. In certain embodiments the blocking ring is slidably displaceable in axial direction relative to the display member at least to a predefined or limited extent. The blocking ring comprises at least one blocking element to axially engage with a blocking structure to block and to impede an axial displacement of the dose member from the dose setting position towards the dose dispensing position.

In one embodiment the at least one blocking element can be rigidly or fixedly attached to the blocking ring. It may be an integral component of the blocking ring. The blocking ring as well as the at least one blocking element might be incompressible. The blocking ring as well as the at least one blocking element might be rather stiff and inelastic. In this way the blocking ring and the blocking element may directly engage with the blocking structure. The blocking element and the blocking structure may mutually abut in axial direction. Typically, a distal edge of the at least one blocking element may engage and axially abut with a proximally facing edge of the blocking structure, thereby blocking a distally directed displacement of the blocking ring relative to the blocking structure and hence relative to the inner body. In this way a distally directed displacement of the blocking ring and also of the dose member, which is at least unidirectionally engaged thereto in the axial distal direction can be effectively prevented.

In other embodiments the blocking element and the blocking ring may be integrally formed but at least one of the blocking ring and blocking element itself or a portion interconnecting the blocking element and the blocking ring is flexible and hence elastically deformable. An elastic deformation on a portion interconnecting the blocking ring and the blocking element may allow and support a displacement of the blocking element relative to the blocking ring.

Switching of the drive mechanism from a dose setting mode into a dose dispensing mode by depressing the dose member in distal direction from the dose setting position towards the dose dispensing position is effectively blocked. Hence, when the blocking ring with its at least one blocking element engages with the blocking structure on the outer circumference of the inner body the drive mechanism and hence the entire drug delivery device cannot be switched into a dose dispensing mode. Dose dispensing is therefore blocked and impeded.

In one embodiment the at least one blocking element is integrally formed with the blocking sleeve. The blocking sleeve as well as the majority of the other components of the drive mechanism are configured as injection molded plastic components. In this way even a rather complex geometric structure of the blocking sleeve and of all the further components can be manufactured with high precision at moderate costs and in large quantities.

The drive mechanism is configured such that application of distally directed thrust to the dose member leads to a distally directed displacement thereof only when the clutch between the dose member and the display member is released so that a display member is free to rotate relative to the dose member. During dose dispensing the dose member is rotationally fixed relative to the inner body and hence to the housing. It is purely axially displaceable relative to the inner body and hence to the housing during a dose dispensing procedure. In order to release and to disengage a torque transferring clutch between the dose member and the display member a small but distinct axial displacement of the dose member relative to the display member is required. As long as the blocking element is engaged with the blocking structure and axially abuts with the blocking structure an axial displacement of the dose member relative to the display member to such a degree that the clutch therebetween would release is effectively prevented. As long as the blocking element is in axial engagement or abutment with the blocking structure a distally directed displacement of the dose member relative to the display member is effectively impeded and the clutch between the dose member and the display member is prevented from disengaging.

Depending on the geometric design and extension of the blocking structure, dose dispensing can be effectively blocked for a predefined range of dose sizes. In this way, minimum and maximum thresholds can be defined between which dose dispensing is effectively blocked and prevented. A minimum threshold may define a maximum dose value for a priming procedure, e.g. 2 or 3 IU. A maximum threshold could define a minimum dose size, hence a dose size that has at least to be dispensed by the drive mechanism in order to ensure sufficient delivery of e.g. one element of a combined drug to obtain a desired therapeutic effect.

The geometric design of the blocking structure may also define only single dose values that may be dispensable with the drive mechanism and with the injection device. Alternatively, the mutual interaction between the blocking structure and the dose member may be configured such that only particular sequential or non-sequential set of dose values are dispensable. It is conceivable, that the drive mechanism only allows setting and subsequent dispensing of a sequential range of doses, such as 10 IU, 11 IU, 12 IU or a non-sequential range of doses, such as 10 IU, 13 IU, 23 IU, etc.

For some applications it may be of particular benefit to offer an injection device that allows delivery of only one fixed dose value but that also permits a 'priming' operation to be undertaken before each dose is administered. The device and its drive mechanism may be of further use for such therapies in which a range of discrete, non-sequential doses of a medicament may be required. For example a range of doses may be needed to satisfy therapeutic needs of different user groups or to allow individual users to deliver a different dose at different times of the day, e.g. morning and evening.

All these different demands can be easily fulfilled by the specific shape, design and geometry of the blocking structure on the outer circumference of the inner body. A general behavior of the drive mechanism and hence of the respective injection device may be individually switched and adapted to different requirements simply by exchanging only the inner body whilst leaving all other components of the drive mechanism unchanged. This is of particular benefit from a manufacturer's point of view. By means of modifying only one of a plurality of components of a drive mechanism the general functionality and dispensing behavior of the drive mechanism can be changed.

According to another embodiment the blocking structure comprises a blocking thread on the elongated shaft. It is located on the outer circumference of the elongated shaft. The blocking thread may extend between convolutions of the outer thread of the inner body. In further embodiments the blocking thread is located axially offset from the outer thread of the shaft. It may be axially separated from the outer thread of the shaft. The blocking structure or blocking thread may be located at a proximal section of the elongated shaft while the outer thread may be located at a distal section of the outer shaft. The blocking thread and the outer thread may be axially non-overlapping and may be axially separated by a predefined non-zero distance.

The blocking thread and the outer thread have the same pitch. Since the blocking thread and the outer thread have the same pitch and since the blocking thread and the outer thread are axially offset the blocking element remains in its blocking position during engagement with the blocking thread when the display member is subject to a helical rotation relative to the inner body during a dose dialing operation. The radial extension of the blocking structure and hence of the blocking thread may be substantially equal to the radial extension of the outer thread.

Since the blocking structure and the outer thread have the same pitch a rotation of the dose member relative to the housing and hence relative to the inner body for setting or dialing of a dose will be always possible. As long as the dose member is in a dose setting position the geometry and design of the at least one blocking element and the blocking structure is such, that the blocking element may pass along or slide along the blocking structure in accordance to the helical motion of the dose member relative to the inner body. While in the dose setting position and when dialing or setting a dose of a particular size the at least one blocking element is located proximally from a proximal edge of the blocking structure. The at least one blocking element may even gently touch or gently slide along a proximal edge of the blocking structure as long as the dose member is in its dose setting position.

A distally directed displacement of the dose member relative to the display member for switching from the dose setting position towards the dose dispensing position then leads to an axial engagement of the at least one blocking element with the blocking structure. The at least one blocking element and the blocking thread substantially overlap in the radial direction as seen in an axial projection. Hence, the at least one blocking element enters the free space between two consecutive convolutions of the blocking thread as the blocking ring and the display member are rotated or dialed for setting of a dose. Due to the axial abutment between the at least one blocking element and the blocking thread a distally directed displacement of the dose member is impeded.

Since the blocking thread and the outer thread have the same pitch the blocking functionality provided by the blocking element and the blocking structure is idle as long as the dose member is rotated relative to the inner body in accordance with the threaded engagement of inner body and display member.

According to another embodiment the blocking structure comprises at least two spiral-shaped blocking segments separated in a tangential direction by at least one gap. The at least one gap has a tangential width or size that is larger than or equal to the tangential width or size of the blocking element. In other words, the at least one gap intersects the blocking thread. The blocking thread may even be constituted by several or by a multitude of blocking segments. In other words, the blocking segments are only portions or segments of the blocking thread that are separated by defined gaps. The position and size of the gaps define the dose sizes or a range of dose sizes for which the drive mechanism is switchable from a dose setting position into a dose dispensing position.

The position and size of the gaps therefore define those doses and dose ranges for which application and administering of the medicament is supported and allowable. Since the tangential or circumferential size of the at least one gap is larger than or equal to the tangential size of the at least one blocking element the blocking element is able to pass through the respective gap only if the dose member is in a helical position that corresponds to a supported and allowable dose size. In such a configuration the at least one blocking element is axially aligned with or overlaps with the at least one gap but is located proximally from the blocking segment that is located tangentially adjacent to said gap. Due to the fact that a tangential size or extension of the at least one blocking element is smaller than or equal to the tangential or circumferential size of the at least one gap a smooth axial and distally directed displacement of the dose member relative to the inner body is supported and allowed.

Consequently, the dose member is then displaceable in the distal direction to such a degree that the clutch between the dose member and the display member is opened and released. The drive mechanism is then switched into the dispensing mode in which the dose member is purely axially and distally displaceable and in which the rotational coupling between the dose member and the display member is suspended thus allowing the display member to rotate in a dose decrementing direction, hence in a direction of rotation opposite to a dose incrementing dialing motion for setting of a dose. With the clutch disengaged or released the dose member and the display member may still be at least coupled in axial direction. A distally directed displacement or sliding motion of the dose member is then transferred to the display member, which due to a permanent threaded engagement with the inner body starts to rotate in the dose decrementing direction.

According to a further embodiment the blocking ring at least partially encloses the inner body and the at least one blocking element protrudes radially inwardly from a sidewall of the blocking ring. The radially inwardly directed extension of the at least one blocking element substantially coincides or corresponds with the radial position and dimensions of the blocking structure. The radial size of the at least one blocking element is small enough to enter the free space between the convolutions of the helical blocking thread. In this way an effective blocking of a distally directed displacement of the blocking ring and hence of the dose member can be impeded as long as the blocking element overlaps in a tangential and radial direction with a blocking segment of the blocking structure as seen in an axial projection. Only when the at least one blocking element fully coincides with a gap of the blocking structure a distally directed displacement of the blocking ring and hence of the dose member relative to the inner body and relative to the display member or relative to a part of the display member that is threadedly engaged with the inner body is allowed and supported, thereby disengaging the clutch between the dose member and the display member.

It is further conceivable that the blocking ring comprises several blocking elements located on the inside of the blocking ring. A multitude of blocking elements can be arranged in a common lateral plane perpendicular to the longitudinal extension of the blocking ring. In other embodiments various blocking elements may be arranged axially offset. In particular embodiments there are provided at least three or four blocking elements on the inside of the blocking ring. Typically, the blocking elements are equidistantly separated around the inner circumference of the blocking ring. Accordingly, the blocking structure may comprise not only one but several blocking threads that are nested relative to each other.

It is conceivable that all blocking threads of a plurality of blocking threads are identical and that the blocking threads are circumferentially offset in accordance with the circumferential offset of the respective blocking elements of the blocking ring. In this way numerous blocking elements may simultaneously engage with numerous blocking threads when the drive mechanism is in a blocking configuration. When in a release configuration, in which dispensing of a dose is allowed and supported all blocking elements are aligned and overlap with respective gaps of the blocking thread. By having a plurality of blocking elements on the sidewall of the blocking ring an axial load applied to the blocking ring is homogeneously transferable into the blocking structure and hence into the blocking thread and into its various blocking segments. In this way, the axial load to be transferred by the blocking ring can be somewhat homogeneously transferred to the inner body and can be hence homogeneously counteracted by the inner body.

The total axial load present to the dose member and hence to the blocking ring may be distributed among the various blocking elements that are simultaneously engaged with respective blocking segments of the blocking structure. The mechanical or axial load acting on each one of the blocking elements can therefore be reduced. Hence, the blocking elements will be less prone to damage or fracture if a mechanical load above a certain threshold should be applied to the dose member or to the blocking ring.

In another embodiment the blocking ring encloses at least an axial section of the display member or a part of the display member. In this way the blocking ring may be axially guided by the display member located radially inside the blocking ring. In other words by enclosing at least an axial section of the display member the blocking ring can be fixed and guided by the display member.

According to another embodiment the at least one blocking element extends radially inwardly through an aperture in a sidewall of the display member. In this way the blocking ring also encloses at least a portion of the display member or a part thereof. By reaching through the aperture of the display member the blocking ring can be arranged on the outer circumference of the display member. In this way a nested arrangement of the blocking ring and the display member is provided and the blocking ring is enabled to directly engage with the blocking structure on the outer circumference of the inner body.

By means of the at least one blocking element extending through the sidewall of the display member a rotational engagement and rotational fixing of the blocking ring and the display member can be obtained. Here, the circumferential width of the aperture in the sidewall of the display member closely matches the circumferential or tangential width of the at least one blocking element. Then the blocking ring and the display member are permanently rotationally locked by means of the blocking element or by means of several blocking elements. By means of the at least one blocking element and the correspondingly-shaped aperture a positive rotational engagement between the blocking ring and the display member can be obtained.

The at least one blocking element and the at least one correspondingly-shaped aperture may provide a snap-fit engagement of the blocking ring and the display member. If the blocking ring is provided with several blocking elements, the display member comprises a respective number of apertures in its sidewall to receive the respective blocking elements. This leads to a slack-free and rather rigid rotational connection between the blocking ring and the display member. The at least one blocking element therefore has a double function. It provides axial engagement with limited permissible relative axial travel between the blocking ring and the blocking structure and it provides a rotational engagement between the blocking ring and the display member.

The at least one aperture of the display member may comprise an axial elongation that is substantially larger than the respective axial length or axial extension of the correspondingly-shaped blocking element of the blocking ring. In this way an axial sliding displacement between the blocking ring and the display member is provided. In situations wherein the at least one blocking element aligns with a gap of the blocking structure the blocking ring is then axially displaceable relative to the display member in order to disengage and to release the clutch between the dose member and the display member or between a driver of the drive mechanism and the display member.

In another embodiment the dose member comprises a dose button and an elongated tubular dose sleeve. The dose button is axially fixed to a proximal end of the dose sleeve. The dose button may also be configured as a dose dial for setting and hence dialing of a dose. The dose button forms a proximal end of the drive mechanism and of the injection device. For the purpose of dose setting the dose button is rotatable in both dose incrementing and decrementing directions. For dose dispensing the dose button is depressible in the distal direction, e.g. when a user applies distally directed thrust to the dose button. It is typically the tubular dose sleeve that is axially engageable or which is optionally permanently engaged with the blocking ring. The dose sleeve and the dose button may be rotationally decoupled. In other embodiments the dose sleeve and the dose button can be rotationally locked. It is even conceivable, that the dose button and the dose sleeve are integrally formed.

Hence, the dose sleeve may comprise a dial portion at its proximal end that is either integrally formed with a planar portion of the dose button or which is configured to receive a planar shaped proximal end of the dose button. In embodiments where the dose button and the dose sleeve are rotationally locked the dose member is rotationally decoupled from the blocking ring. Hence, the blocking ring is free to rotate relative to the dose member at all times. Such an embodiment is beneficial since the dose member is rotationally fixed during dose dispensing, whilst the blocking ring is subject to rotation during dose dispensing. With the dose sleeve rotationally fixed to the dose button the dose sleeve will be subject to a purely distally directed translational movement during dose dispensing. Hence, it will not rotate during dose dispensing. This may reduce a risk, that the user inadvertently stalls the device during delivery of a dose.

According to another embodiment the dose sleeve and hence the dose member comprises a distal face to axially abut with a proximal face of the blocking ring. The distal face of the dose sleeve may be a distal end face and may be located at the distal end of the dose sleeve. Correspondingly, also the proximal face of the blocking ring may be a proximal end face of the blocking ring. The blocking ring and the dose sleeve typically comprise somewhat identical radial dimensions. Hence, a sidewall of the dose sleeve near its distal end overlaps in the radial direction with a sidewall at the proximal end of the blocking ring so as to provide a substantial mutual abutment in axial direction. By means of distal and proximal faces of the dose sleeve and the blocking ring the dose sleeve and hence the dose member is configured to displace the blocking ring in the distal direction, thereby also switching the drive mechanism from the dose setting mode into the dose dispensing mode.

The mutual axial abutment between the dose sleeve and the blocking ring may be configured as a simple abutment. Hence, an axial displacement of the dose sleeve only has an effect on the blocking ring when the dose sleeve is displaced in distal direction. Apart from the mutually corresponding distal and proximal faces the dose sleeve and the blocking ring are void of any further axial coupling. In this way a returning of the dose sleeve and hence of the dose member from the dispensing position towards the dose setting position, typically in proximal direction, has no direct effect on the axial position of the blocking ring. In this way the dose member is enabled to return into its proximal dose setting position when a dose dispensing procedure is interrupted or paused at a dose size that is outside the range of allowable dose values.

By only having a simple and hence unidirectional abutment between the dose sleeve and the blocking ring the dose member is displaceable in the proximal direction independent of a release or blocking configuration of the blocking ring with regard to the blocking structure. So even if a dose dispensing procedure is paused, the user would then be able to adjust the dose selection before a previously set dose has been completely dispensed.

In addition and since there is no bi-directional axial coupling between the dose member and the blocking ring, misuse loads applied to the dose member, i.e. dragging or pulling the dose member in proximal direction cannot be transferred to the blocking ring at all. Such mechanical loads applied to the dose member in the proximal direction are totally decoupled from the blocking ring. A danger or likelihood of breakage or fracture of the at least one blocking element when in blocking configuration with the blocking structure can be effectively reduced or eliminated.

According to another embodiment the dose sleeve and hence the dose member is axially fixed to the blocking ring. An axial mutual fixing between the dose sleeve and the blocking ring can be attained by a clip joint or some other positively engaging interconnection that allows and supports a rotation of the blocking ring relative to the dose sleeve. Hence, the dose sleeve and the blocking ring may comprise mutually corresponding snap or clip features at their distal and proximal ends, respectively.

According to another embodiment the blocking ring is displaceable in the distal direction relative to the display member against the action of a spring element. In this way the blocking ring is axially biased in the proximal direction. It is hence permanently urged in the proximal direction so that its at least one blocking element is normally located on a proximal side of the blocking structure's blocking thread or blocking segments. The spring element is of particular use for embodiments in which the dose sleeve only axially abuts with the blocking ring, wherein the dose sleeve is not permanently axially fixed to the blocking ring. So if dose dispensing has been completed the at least one blocking element is always aligned with a gap of the blocking structure thus allowing the blocking ring and the dose member to return into the initial and proximal dose setting position.

While the dose member and hence the dose sleeve is pushed in the proximal direction under the action of a clutch spring the blocking ring is individually urged in proximal direction under the effect of the spring element as mentioned above. In this way it is guaranteed that the blocking ring also returns into its initial axial position, in which a repeated dose setting and dialing of the dose member and the display member is allowable.

According to a further embodiment the blocking ring and the dose sleeve are rotationally decoupled. Hence, the blocking ring is free to rotate relative to the dose member at all times. Therefore, the dose sleeve will not rotate during dose dispensing. This may reduce a risk, that the user inadvertently stalls the device during delivery of a dose.

In another embodiment the blocking ring comprises an annular-shaped ring portion and at least one arched portion located axially offset to the ring portion. The arched portion comprises or forms a curved cantilever portion. The at least one blocking element is located at a free end of the curved cantilever portion. The curved cantilever portion typically extends in tangential direction and comprises a semi-circular or circular sectional shape. It is conceivable, that several curved cantilever portions extend along the outer circumference of the blocking ring. The at least one blocking element extends radially inwardly from the free end of the curved cantilever portion. The curved cantilever portion forms a flexible arm and e.g. a semi-circular structure which is only fixed with one tangential or circumferential end to the annular ring portion. The ring portion is axially engageable or is in fact axially engaged with the dose member, e.g. via the dose sleeve. The ring portion of the blocking ring may be permanently and bi-directionally coupled to the dose member.

The curved cantilever portion exhibits well-defined flexibility in the radial direction as well as in the axial direction. The curved cantilever portion with the radially inwardly protruding blocking element is displaceable in a radial outward direction as the at least one blocking element engages with the blocking structure. Additionally, when the at least one blocking element engages with the blocking structure, the curved cantilever portion may axially engage with the ring portion and hence it may axially engage with the dose member that is at least in axial abutment with the ring portion. On the outer circumference of the curved cantilever portion there is typically provided a brake surface, e.g. having a friction enhanced surface structure.

When engaging with the blocking structure the curved cantilever portion is urged radially outwardly so as to frictionally engage with an inside facing sidewall section of the housing of the injection device. Since the blocking ring is permanently rotationally fixed to the display member the display member as well as the blocking ring are hindered from rotating relative to the housing and hence relative to the inner body when the at least one blocking element is in axial abutment with the blocking structure. This is of particular benefit for situations where a set dose value is only one increment above or below a dose value that is allowable to be dispensed by the drive mechanism.

In such situations there may be only a rather limited and partial tangential or circumferential radial overlap between the at least one blocking element and the blocking segments of the blocking structure. If at the very beginning of a dose dispensing procedure, which should be blocked by the mutual engagement of blocking ring and blocking structure, the dose member should be subject only to a small rotation, the residual engagement and overlapping of the at least one blocking element with the blocking segment of the blocking structure may become too small to securely prevent and to block the distally directed displacement of the dose member. Also as a result of geometrical tolerances of the various components of the drive mechanism and necessary running clearances therebetween it may happen that the overlap between the at least one blocking element and the blocking structure is reduced to such a degree where there is only insufficient contact area therebetween to prevent the at least one blocking element and the blocking structure from deforming, slipping or disengaging.

Due to the friction brake provided by the at least one curved cantilever portion the blocking ring is immediately hindered in rotation as distally directed thrust is applied to the blocking ring at the beginning of a blocked dose dispensing action. The curved cantilever portion may even be pre-tensed in radial direction so as to smoothly slide along the inner circumference of the housing. If the curved cantilever portion then engages with the blocking structure it is already in mechanical contact with the housing and immediately provides an enhanced friction effect with regard to the housing.

In another embodiment the curved cantilever portion is flexible and exhibits a higher degree of flexibility in a radial direction than in an axial direction. A rather high degree of flexibility and hence a rather low degree of stiffness in the radial direction is beneficial to immediately provide a braking effect at the beginning of a non-allowed or non-supported dose dispensing procedure.

In this way a rotation of the dose member and hence of the blocking ring towards a direction in which the overlap between the blocking elements and the blocking structure is reduced can be effectively be prevented.

In an initial configuration the curved cantilever portion may be substantially axially separated from the ring portion. Apart from a mutual interconnection therebetween there may be located a small axial and tangential recess or gap between the ring portion and the curved cantilever portion. Such an axial gap allows for a limited axial displacement of the curved cantilever portion relative to the ring portion, e.g. so as to smoothly bias the at least one blocking element in the distal direction against the proximal edge of the blocking structure. In this way the blocking element provided at the free end of the curved cantilever portion can be in a slight axial abutment with the blocking structure during dialing of a dose.

According to a further embodiment the drive mechanism comprises a piston rod and a tubular-shaped driver, both extending in the axial direction. The piston rod typically comprises a first outer thread engaged with an inner thread of the inner body. In this way, a rotation of the piston rod in a dispensing direction leads to a distally directed advancing of the piston rod relative to the inner body and hence relative to the cartridge which is axially constrained inside the housing of the injection device. The piston rod may further comprise a second outer thread of opposite hand compared to the first outer thread, wherein the second outer thread is threadedly engaged with an inner thread of the driver. In this way, an axial but non-rotative displacement of the driver in the distal direction induces a rotation of the piston rod which due to the threaded engagement with the inner thread of the inner body advances it in the distal direction during dose dispensing. Hence, during dose dispensing the driver is subject to a distally directed purely translational but non-rotational movement. For dose dispensing the driver is rotationally locked to the inner body. It may be coupled to splines in the inner body so that the driver is prevented from rotating relative to the body but is free to be axially displaced relative to the body during dose dispensing.

In a dose setting configuration the driver may be rotationally locked or coupled to the display member so as to follow the helical motion of the display member relative to the inner body. In dose setting mode, a splined engagement of driver and inner body is abrogated or released.

Instead, the driver is free to rotate in accordance to a helical path that coincides with the threaded engagement of driver and piston rod so that the driver is axially displaceable in proximal direction relative to the inner body and relative to the piston rod, which during dose setting is stationary with regard to the inner body.

By means of the two threads of the piston rod of opposite hand a displacement transition ratio between the distally directed displacement of the driver and the piston rod can be implemented. A rather large axial displacement requiring a rather low dispensing force can therefore be transferred into a rather short displacement of the piston rod with a rather large dispensing force.

According to another embodiment the dose member is permanently splined with the driver. The driver in turn is selectively rotationally lockable to the inner body by displacing the dose member into the dose dispensing position. When the dose member is in dose setting position the driver is no longer rotationally locked to the body but is free to rotate relative to the body, e.g. by means of a clicker detent engagement by way of which the rotation of the driver relative to the body produces an audible and tactile click sound thereby indicating to the user, that subsequent discrete steps of dose setting actually take place.

The driver and the display member may be axially engaged either directly or indirectly via an axial engagement of the dose member with both the driver and the display member.

When implemented as a mechanism for a disposable injection device the dose member and the driver may be permanently rotationally locked. For instance, the dose member and driver may be splined together so that the dose member is prevented from rotating during dose dispensing by the driver being rotationally locked to the inner body.

According to another embodiment the driver is rotationally locked to the dose member and wherein the dose member is rotationally engageable with the display member by means of a clutch. Typically, the driver is directly and permanently rotationally engaged with the dose member. The clutch is operable to:

rotationally engage the dose member and the display member when the dose member is in the dose setting position and further to rotationally release the display member from the dose member when the dose member is in the dose dispensing position.

A rotational engagement means a torque transferring engagement between the respective components. With this embodiment the driver is permanently rotationally locked to the dose member and the dose member is selectively rotationally engageable with the display member via the clutch and e.g. via a clutch sleeve.

By means of the clutch the drive mechanism is switchable between a dose setting or dose dialing mode and a dose dispensing mode. During dose dialing or dose setting the clutch is closed so that any rotation of the dose member and hence of the dose dial or dose button thereof equally transfers to the display member. During dose dispensing and with the clutch disengaged the display member is free to rotate back into its initial position while the dose member may be subject to a purely distally directed sliding displacement without rotation. During dose setting and in dose setting mode the dose member, the dose dial as well as the display member are subject to a helical motion with regard to the housing or with regard to the inner body. During dose dispensing the display member is subject to a dose decrementing and oppositely directed helical motion while the dose member and hence the dose dial or the dose button, typically depressed by a thumb of the user, is subject to a pure axial sliding motion. The dose dial, the dose member and the drive sleeve are rotationally fixed to the housing or to the inner body as the drive mechanism is switched into the dose dispensing mode.

In a dose setting configuration the driver may be rotationally locked or rotationally coupled to the display member so as to follow the helical motion of the display member relative to the inner body. In dose setting mode, a splined engagement of driver and inner body is abrogated or released. Instead, the driver is free to rotate in accordance with a helical path that coincides with the threaded engagement of driver and piston rod so that the driver is axially displaceable in proximal direction relative to the inner body and relative to the piston rod, which during dose setting is stationary with regard to the inner body.

By means of the two threads of the piston rod of opposite hand a displacement transition ratio between an axial distally directed displacement of the driver and the piston rod can be implemented. A rather large axial displacement requiring a rather low dispensing force can therefore be transferred into a rather short displacement of the piston rod with a rather large dispensing force.

According to another embodiment the dose member is permanently splined with the driver. The driver in turn is selectively rotationally lockable to the inner body by displacing the dose member into the dose dispensing position. When the dose member is in dose setting position the driver is no longer rotationally locked to the body but is free to rotate relative to the body, e.g. by means of a clicker detent engagement by way of which the rotation of the driver relative to the body produces an audible and tactile click sound thereby indicating to the user, that subsequent discrete steps of dose setting actually take place.

The driver and the display member may be axially engaged either directly or indirectly via axial engagement of the dose member with both, the driver and with the display member.

The clutch between display member and dose member is released when the dose member is switched or depressed into its dispensing position. In the dispensing position or dispensing configuration the dose member is axially distally displaceable in a non-rotative way relative to the inner body. Simultaneously, the dose member, the driver and the display member are axially engaged. A depression of the dose member or exertion of a distally directed dispensing force onto the dose member therefore leads to a distally directed helical twisting motion of the display member together with a distally directed non-rotating translation of the driver to induce a driving torque to the piston rod.

When implemented as a mechanism for a disposable injection device the dose member and the driver may be permanently rotationally locked. For instance, the dose member and driver may be splined together so that the dose member is prevented from rotating during dose dispensing by the driver being rotationally locked to the inner body.

In another aspect the invention further relates to an injection device for setting and dispensing of a dose of a medicament. The injection device is typically configured as a pen-type injector. It comprises an elongated housing to accommodate a drive mechanism as described above and a cartridge arranged inside the housing and filled with a liquid medicament. The cartridge is typically located within and accommodated by a cartridge holder forming a distal portion of the housing of the injection device. When the injection device is implemented as a disposable device the cartridge holder and the proximal housing component are typically permanently interconnected. This connection is of non-releasable type. Separation of the proximal housing and the cartridge holder requires destruction or breaking of one of these components. When implemented as a reusable device the cartridge holder is releasably connected with the proximal housing part so as to provide access to the cartridge for cartridge replacement as well as to enable a reset operation of the drive mechanism.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention.

Further, it is to be noted, that any reference numerals used in the appended claims are not to be construed as limiting the scope of the invention.

BRIEF DESCRIPTION OF THE DRAWINGS

In the following, embodiments of the drive mechanism and the injection device are described in detail by making reference to the drawings, in which.

DETAILED DESCRIPTION

Figure 1:
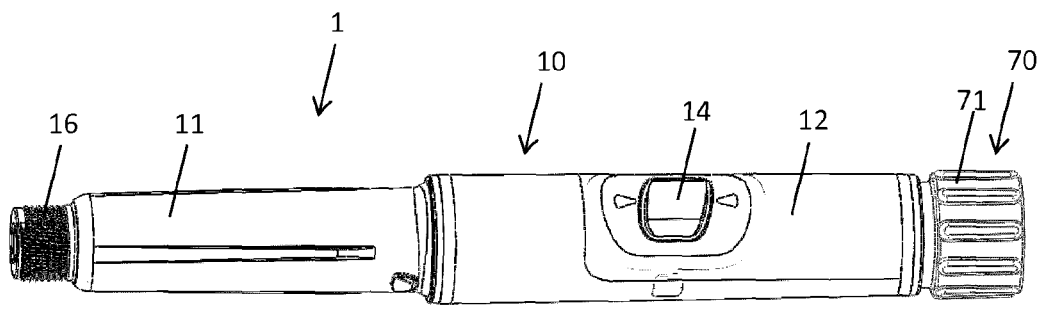
FIG. 1 shows a perspective outer view of the injection device.

FIG. 1 shows a drug delivery device 1 in the form of an injection pen. The device has a distal end, shown as left end in FIG. 1 and a proximal end located at the right hand side FIG. 1.

Figure 2:
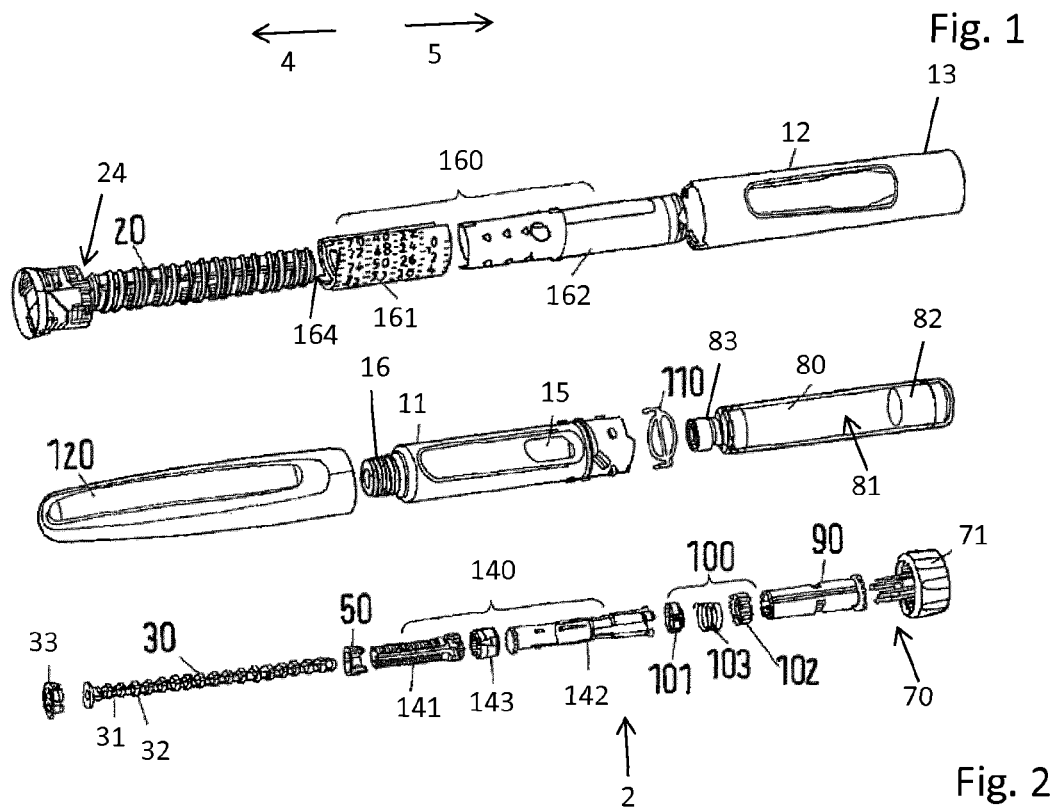
FIG. 2 shows an exploded view of an embodiment of the injection device.
Figure 3:
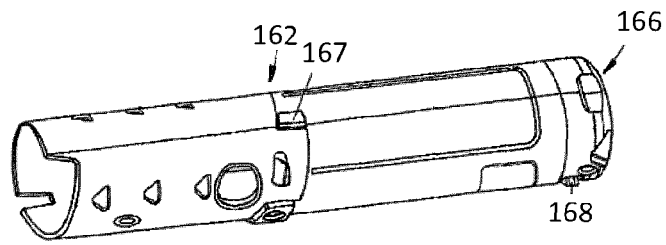
FIG. 3 shows a dial sleeve of the display member according to FIG. 2.

The components or parts of the drug delivery device 1 and its drive mechanism 2 are shown in FIG. 2 in more detail but without showing the blocking ring 180 with blocking elements 182 and without showing the blocking structure 40. The drug delivery device 1 comprises an outer housing part 12, a cartridge holder 11, an inner body 20, a piston rod 30, a driver 140, a last dose nut 50, a display member 160, a dose member 70, a cartridge 80 and a cap 120. Even though not shown in FIG. 2, a needle arrangement comprising a needle hub and a needle cover may be provided as additional components, which can be exchanged. The general concept and structure of the drive mechanism as shown in FIGS. 2 to 18 is similar and partially identical to a re-usable mechanism disclosed in WO 2014/033195 A1, which is incorporated herein by reference. The drive mechanism may be also implemented as a disposable drive mechanism being void of a reset function as disclosed in WO 2014/033197 A1, which is also incorporated herein by reference.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal cap 83 is used to hold the rubber seal in place. The cartridge 80 is provided within the cartridge holder 11 with bearing 33 of piston rod 30 abutting bung 82. FIG. 2 shows the cap 120, which is detachable from the distal end of the device 1, thus giving access to the cartridge holder 11. The cap 120 may be releasably snapped onto the outer housing 10 and can be taken off for use of the device 1.

The outer housing part 12 is a generally tubular element forming a proximal part of the housing 10 of the device 1. A cartridge holder 11 for receiving the cartridge 80 and forming a distal part of the housing 10 is detachably connectable to the proximal housing part 12, which forms an outer body. In one embodiment, the outer housing is transparent, with the outer body 12 being provided with an opaque layer 13. In FIG. 1, the opaque layer 13 covers most of the outer body 12 with the exception of a transparent window 14. Apertures 15 may be provided in the cartridge holder 11. Further, at its distal end the cartridge holder 11 has a thread 16 or the like for attaching the needle hub 2.

Figure 17:
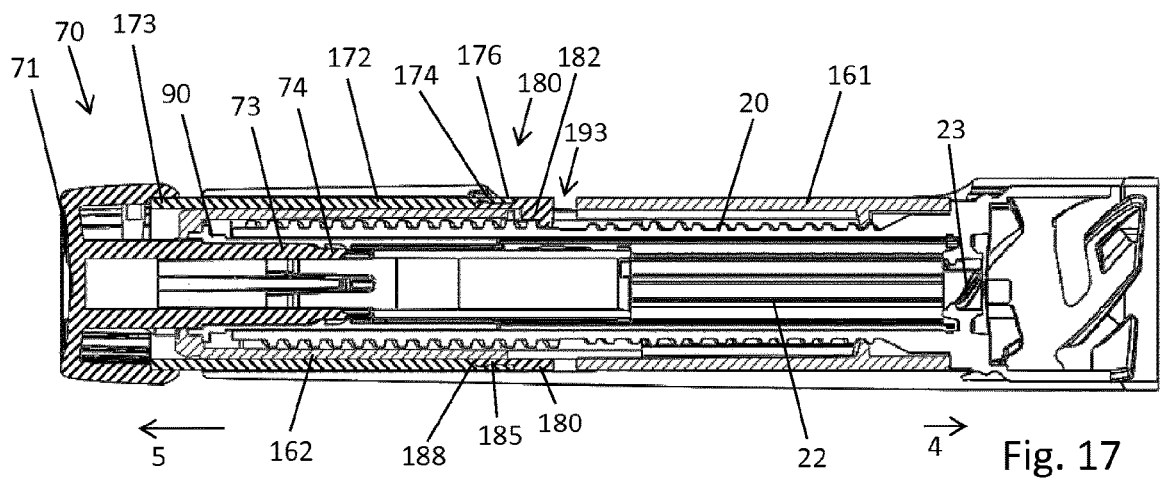
FIG. 17 is a longitudinal cross-section through the inner body with the dose member, the display member and the blocking ring attached thereto.
Figure 18:
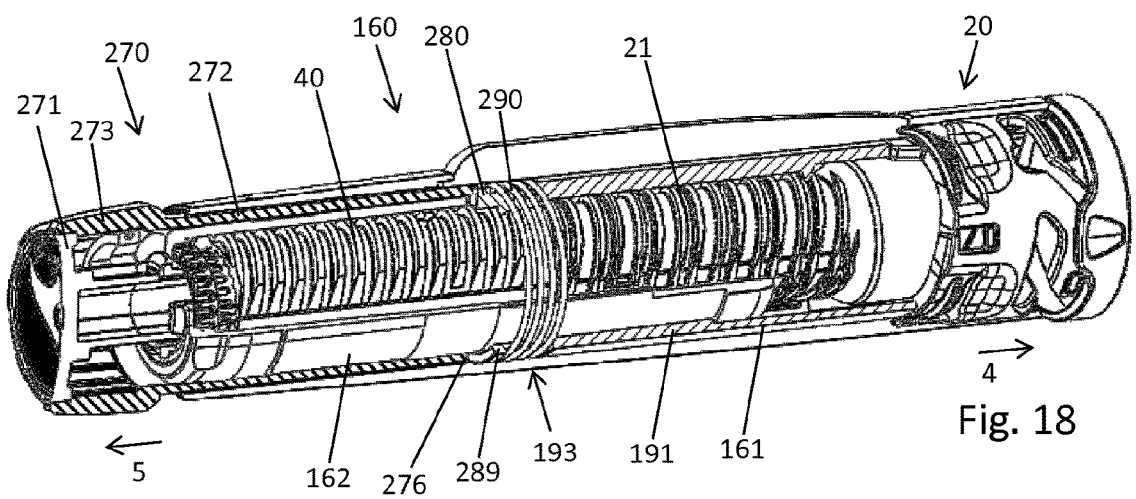
FIG. 18 is a partial cut and perspective view of the proximal end of another embodiment of the drive mechanism.

The inner body 20 is a generally tubular element having different diameter regions. The inner body 20 is received in the outer body 12 and permanently fixed therein to prevent any relative movement of the inner body 20 with respect to the outer body 12. An external thread 21 is provided on the outer surface of a shaft portion 20a of the inner body 20. Further, splines 22 are provided on the inner surface of the inner body 20 which are shown in FIG. 17. The inner body 20 has near its distal end an inner thread 23.

The piston rod 30 is an elongated element having two external threads 31, 32 with opposite hand which overlap each other. One of these threads 31 engages the inner thread 23 of the inner body 20. A disk-like bearing 33 is provided at the distal end of the piston rod 30. The bearing 33 may be attached to the piston rod 30 as a one-piece component via a predetermined breaking point. This allows that the bearing 33 is separated from the piston rod 30 such that the bearing 33 remains seated on the distal end of the piston rod 30 to allow relative rotation between the bearing 33 and the piston rod 30.

In this embodiment, the driver 140 is a generally tubular element having in the embodiment shown in the Figures three components 141, 142, 143 which are depicted in FIGS. 2, 5, 6 and 8 in more detail. The driver 140 comprises a distal drive sleeve 141, a proximal drive sleeve 142 and a coupler 143. The distal drive sleeve 141 comprises an inner thread 142a that engages with the piston rod thread 32 to drive the piston rod 30 through the inner body 20 during dose delivery. The distal drive sleeve 141 is also permanently connected to the coupler 143 which in turn is releasably engaged through reset clutch features to the proximal drive sleeve 142. The two halves of the drive sleeve 141, 142 are rotationally and axially connected during dialing and dispense, but are decoupled rotationally during device reset so that they can rotate relative to each other.

Figure 8:
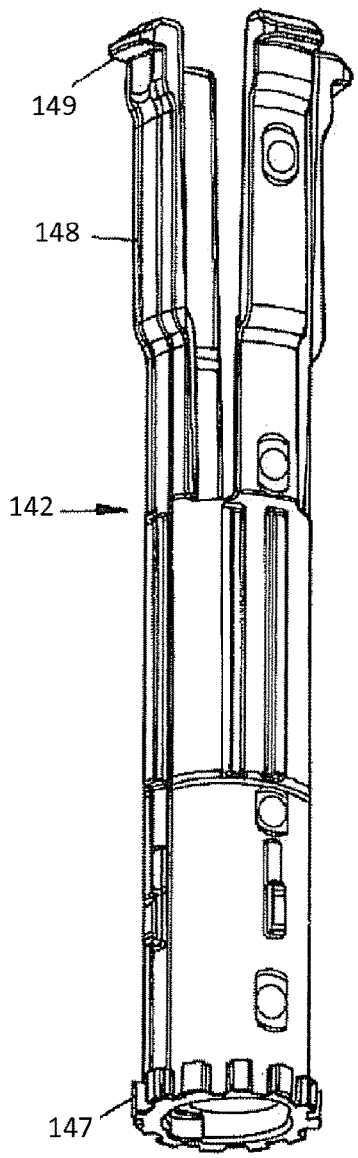
FIG. 8 shows a proximal driver part.
Figure 9:
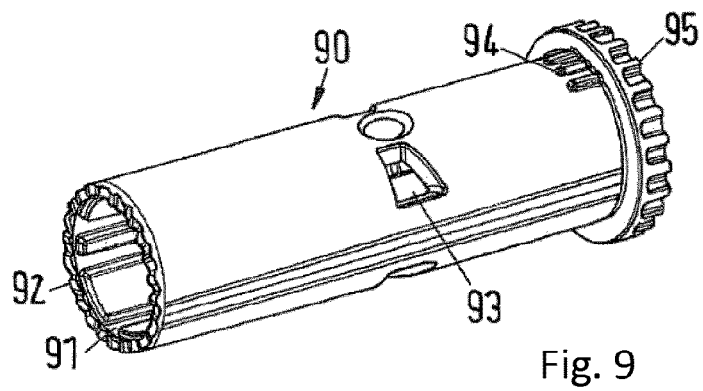
FIG. 9 shows a clutch sleeve.
Figure 10:
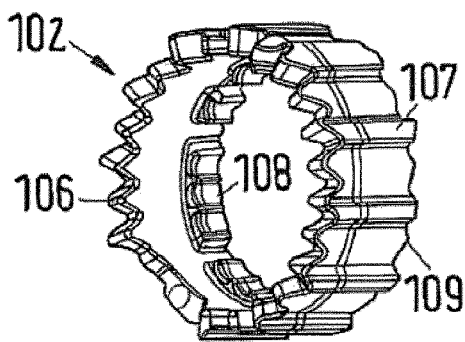
FIG. 10 is an isolated view of a proximal clicker part.
Figure 11:
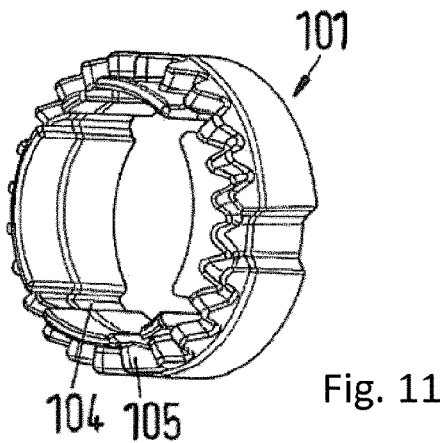
FIG. 11 is an isolated view of a distal clicker part.

The proximal drive sleeve 142 shown in FIG. 8 supports components of a clicker 100 and sleeve shaped clutch sleeve 90 and transfers rotational movement from the dose member 70 to the coupler 143 and distal drive sleeve 141. Teeth features 147 located at the distal end of proximal drive sleeve 142 engage with the reset clutch features on the coupler 143 to connect both halves of the drive sleeve during dialing and dispense. During reset these teeth 147 disengage.

Several splines are provided on the outer surface of proximal drive sleeve 142 engaging with a distal clicker part 101, preventing relative rotation during dialing and dispense. Further splines, which are located in the middle region of proximal drive sleeve 142, engage with the clutch sleeve 90 component. They may be arranged to be non-rotationally symmetric so that the various clicker components cannot be assembled accidentally upside down.

The proximal portion of proximal drive sleeve 142 has four arms or fingers 148. A hook-like bearing surface 149 exists on the underside of flange segments on the end of the flexible fingers 148 as seen in FIG. 8. The flexible fingers 148 are separated with gaps or slots that make space for the dose member 70 to snap to the clutch sleeve 90 and also enable these fingers to flex inwards during assembly of the proximal drive sleeve 142 to a dial sleeve 162. After assembly the hooks 149 retain the proximal drive sleeve 142 relative to the dial sleeve 162 under the reaction force from the spring 103.

During dispense the dose member 70 depresses the spring 103 via the clutch sleeve 90 and the clicker components and this spring 103 is reacted through the coupler 143 to the proximal drive sleeve 142 which then through bearing surfaces 149 applies axial load to the dial sleeve 162. This axial load drives the dial sleeve 162 and hence a number sleeve 161 along the helical thread of the inner body 20, back into the body of the device, until the zero dose stop faces 164 on the number sleeve 161 contact the inner body 20.

Figure 6:
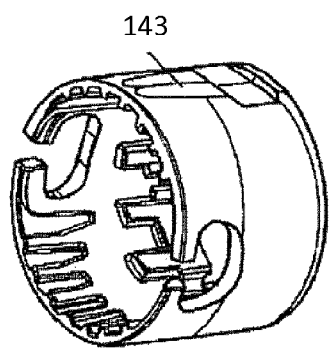
FIG. 6 shows an isolated view of a coupler.
Figure 7:
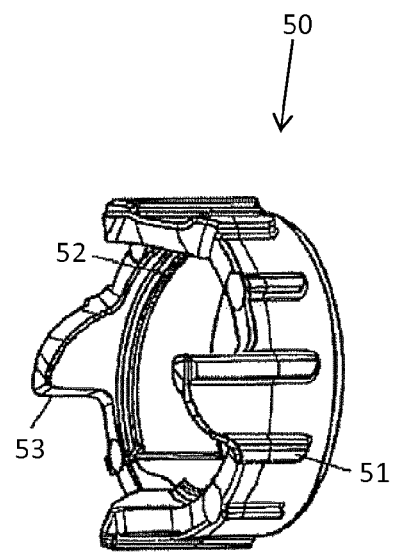
FIG. 7 shows an isolated view a last dose nut.

The coupler 143 shown in FIG. 6 rotationally couples the two halves of the drive sleeve 140 together during dialing and dispense, whilst allowing them to de-couple during reset. The coupler 143 has to also transfer the last dose stop load from the proximal drive sleeve 142 to the distal drive sleeve 141. Two sets of teeth are provided in the coupler 143 for engaging teeth 146 and teeth 147, respectively. The coupler 143 is snapped onto distal drive sleeve 141 allowing limited relative axial movement with respect to the proximal drive sleeve 142.

The last dose nut 50 is provided between the inner body 20 and the distal drive sleeve 141 of driver 140. Stop faces 53 are located on the proximal face of last dose nut 50 to limit the number of units that can be dialed if the stop faces 53 contact stops 145 of distal drive sleeve 141. The function of the last dose nut 50 is to prevent the user from dialing beyond a finite amount. This limit is based on the dispensable volume of the cartridge 80 and when reached, the user must replace the cartridge 80 and reset the device.

External ribs 51 of the last dose nut 50 engage splines 22 of inner body 20. An internal thread 52 of the nut engages the external thread 144 of distal drive sleeve 141. As an alternative, splines and ribs could be provided on the interface between the nut 50 and the driver 140 and threads could be provided on the interface between the nut 50 and the inner body 20. As a further alternative, the nut 50 may be designed as e.g. a half nut.

The display member 160 is a generally tubular element which is composed of a number sleeve 161 and dial sleeve 162 which are snapped together during assembly to axially and rotationally constrain these two components, which thus act as a single part. The dial sleeve 162 is assembled to the number sleeve 161 such that once assembled, no relative movement is allowed. The parts are made as separate components to enable both molding and assembly. Also, whereas the number sleeve 161 is preferably white to give contrast for the e.g. black dose numbers, the dial sleeve 162 color can be chosen to suit the aesthetics or perhaps to distinguish the drug type.

At the proximal end, the dial sleeve 162 has internal clutch features 165 that engage with the clutch sleeve 90 during dialing and disengage from the clutch during dispense. These clutch features 165 rotationally lock the dial sleeve 162 to the clutch sleeve 90 during dialing and when the zero and maximum dose stops are engaged. When the dose member 70 is depressed these clutch features disengage to allow the clutch sleeve 90 to move axially whilst the dial sleeve 162 and number sleeve 161 spin back to the zero unit start position.

Figure 4:
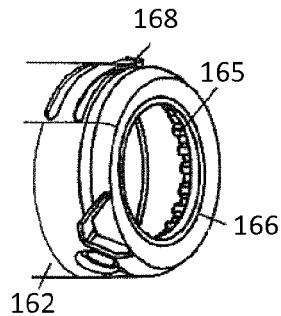
FIG. 4 shows a proximal end of the display member according to FIG. 2.
Figure 5:
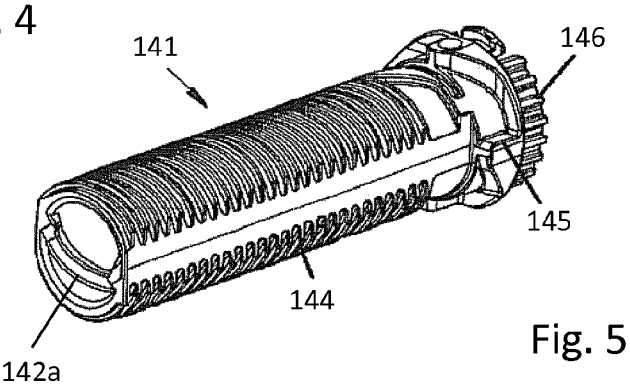
FIG. 5 is an isolated view of a distal driver part according to FIG. 2.

The dial sleeve 162 rotates out during dialing through its engagement with the clutch sleeve 90 and number sleeve 161, and rotates back in during dispense under the axial force applied by the proximal drive sleeve 142 to a flange-like bearing face 166 on the proximal end of the dial sleeve as shown in FIG. 4. This bearing face 166 engages with the flexible arms 148 of the proximal drive sleeve 142 during dispense. Two diametrically opposite faces 167 may engage with the outer body 10 when the maximum dose has been dialed, to form the maximum dose stop faces.

A central sleeve-like portion of the dose member 70 is provided with four arms 73 having hook-like snap features 74 at their respective distal ends. The arms 73 form splined surfaces engaging with the clutch sleeve 90 to transfer torque from the dose member 70 through the clutch sleeve 90 to the dial sleeve 162 and proximal drive sleeve 142. The snap features 74 engage apertures in the clutch sleeve 90 and are designed with angled undercut faces to maintain engagement when an axial load is applied to pull the dose member 70 out of the pen body 10. The space between arms 73 defines pockets giving clearance for the flexible arms 148 of proximal drive sleeve 142 to slide freely relative to the dose member 70 and clutch sleeve 90 when the dose member 70 is depressed to release the clutch during dose dispense.

The tubular clutch sleeve 90 is provided between the display member 160 and the dose member 70. The clutch sleeve 90 is fixed relative to and retains the dose member 70 and together they travel axially relative to the proximal drive sleeve 142 when the dose member 70 is depressed during dispense, disengaging the clutch teeth 95 from the dial sleeve clutch teeth 165. The clutch sleeve 90 also transfers torque from the dose member 70 to the proximal drive sleeve 142, and the dialing and zero and maximum dose stop loads from the dose member 70 via the clutch teeth to the dial sleeve 162 and number sleeve 161.

Splines 91 provided on an inner surface of the clutch sleeve 90 engage with the proximal drive sleeve 142. At the distal end face, clutch biasing teeth 92 are provided which mate with similar teeth 109 on the proximal clicker part 102 to ensure that in the unrestrained button out position (dialed dose) the clutch is biased in rotation to the proximal clicker part 102 under the biasing action of the clutch spring 103 thus ensuring that the dose number shown on the display member is correctly and unambiguously displayed to the user. The teeth 92 are shallow in height to prevent the proximal clicker part 102 from engaging with splines on the proximal drive sleeve 42 during dialing. Four snap apertures 93 serve to retain the snap features 74 of the dose member 70. Near its proximal end, the clutch sleeve 90 has splines 94 which at the end of dispense with the dose member 70 depressed, lock to the inner body 20 to prevent the user from rotating the dose member 70 below the zero dose position.

Clutch teeth 95 engage with clutch teeth 165 of the dial sleeve 162 to rotationally couple the dose member 70 via the clutch to the number sleeve 161. During dispense the clutch sleeve 90 is moved axially and distally so as to disengage these clutch teeth 95 releasing the dial sleeve 162 to rotate back into the device whilst the clutch sleeve 90 and hence driver 140 move axially to dispense the dose.

The clicker 100 comprises a distal clicker part 101, a proximal clicker part 102 and a spring 103. The spring 103 serves to bias the dose member 70 out so that at the end of a dose the dose member 70 moves axially in the proximal direction, re-engaging the clutch sleeve 90 with the dial sleeve 162 ready for dialing. Further, it provides the spring force for the clicker components to provide audible and tactile feedback to the user and also provides detent positions for the number sleeve 161. In addition, it holds the two halves of the drive sleeves 141, 142 in rotational engagement during dialing and dispense, whilst allowing them to disengage during device reset.

The distal clicker part 101 is permanently splined to the proximal drive sleeve 142 and engages with the proximal clicker part 102 which in turn is splined and hence rotationally locked but axially displaceable to the inner body 20. During dialing when the driver 140 is rotated relative to the inner body 20, the two clickers 101, 102, rotate relative to each other under the compression force of the clutch spring 103. This force acting through the clicker teeth formed on the end face of each clicker provides the clicks and also the detent dialing positions During dispense the two clickers 101, 102 are pressed together under the axial dispense load applied by the user to the dose member 70 and this prevents relative rotation between the proximal drive sleeve 142 and inner body 20, driving the piston rod 30 forwards to deliver the dose. The splines 104 on the inner bore rotationally couple the distal clicker part 101 to the proximal drive sleeve 142 at all times, but allow free axial movement when the dose member 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body 20 during both dialing and dispense, providing clicks during dialing and locking the proximal drive sleeve 142 in rotation during dispense. Additional cylindrically shaped splines 108 also couple the proximal clicker part 102 rotationally to the proximal drive sleeve 142 when the dose member 70 is depressed, this preventing the user from dialing past 80 units with the dose member 70 depressed. Proximal clicker part 102, in addition to the primary clicker teeth 106, has clutch biasing teeth 109 on the opposite end face. These teeth mate with similar teeth 92 on the clutch sleeve 90 to ensure that in the unrestrained button out position (dialed dose) the clutch is biased in rotation by the proximal clicker part 102 under the biasing action of clutch spring 103.

The cartridge bias spring 110 is assembled as two components one after the other, the lower first and the upper second. The spring combination serves to apply an end load to the cartridge 80 so as to bias it forwards onto the end face of the ferrule in the cartridge holder 11. This ensures that when the user removes and attaches a needle, the friction between the needle cannula and septum of the cartridge 80 does not move the cartridge 80 axially relative to the cartridge holder 11. The bias spring 110 also acts to provide a force against which the user has to connect the cartridge holder 11 and this may add to the tactile feedback of a bayonet joint between cartridge holder 11 and inner body 20. The spring 100 also serves to eject the cartridge holder 11 if the cartridge holder is not correctly attached in a secure position, highlighting this error to the user.

During dose setting the dose member 70, driver 140 and display member 160 are rotationally locked together via clutch sleeve 90. Further, dose member 70, driver 140 and display member 160 are axially coupled. Thus, these three components wind out of the outer body 12 during dose setting. Clockwise rotation of the dose member 70, i.e. rotation of the dose dial 71 causes the driver 140 to rotate on a helical path and in doing so it advances along the piston rod 30 which remains fixed throughout dialing. The clicker arrangement 100 provides tactile and audible feedback to the user when dialing doses. At the maximum settable dose of 80 units, stop features engage to prevent further dialing.

With the desired dose dialed, the device 1 is ready for dose dispensing. This requires pushing the proximal button portion of the dose member 70 which will result in a disengagement of the clutch sleeve 90 from dial sleeve 162 thus allowing relative rotation between the display member 160 and the dose member 70. In all conditions the driver 140 and the dose member 70 are rotationally locked together by engagement of arms 73 and fingers 148 and by splines 91 engaging corresponding splines on proximal drive sleeve 142. Thus, with the clutch sleeve 90 disengaged dose member 70 and driver 140 are rotationally locked together with the dose member 70, the driver 140 and the display member 160 still being axially coupled.

When dispensing a dose, the dose member 70 and clutch sleeve 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the drive sleeve 140 and clutch sleeve 90 parts of the mechanism are rotationally locked to the inner body 20 and are thus forced to move axially whilst the dial sleeve 162 and number sleeve 161 are free to spin back into the outer housing 10. The interaction of mating threads between the piston rod 30, driver 140 and inner body 20 delivers a mechanical advantage.

In other words, axially advancing driver 40 causes the piston rod 30 to rotate which due to the threaded engagement of piston rod 30 with the inner body 20 advances the piston rod 30. During dose dispensing dispense clicker 168, 71 is active which involves dose member 70 and display member 160. The dispense clicker provides primarily audible feedback to the user that the medicament is being dispensed.

When dispensing of a dose is complete and when the user removes the force from the end of the dose member 70, the clutch spring 103 pushes this dose member 70 proximally, re-engaging the teeth 165 and 95 between the clutch sleeve 90 and the dial sleeve.

Resetting the device starts with removal of the cartridge holder 11 and replacing an empty cartridge with a full cartridge 80. As the cartridge holder 11 is re-attached, the bung of the new cartridge 80 contacts bearing 33, thus pushing piston rod 30 back into the housing. Initially, the piston rod 30 screws into the inner body 20, thereby axially disengaging the coupler 143 from the proximal drive sleeve 142 against the biasing force of spring 103. Once disengaged the coupler 143 is free to start rotating together with distal drive sleeve 141 and continues to do so as the cartridge holder 11 is moved axially into engagement with the inner body 20. Thus, the distal drive sleeve 141 rotates with respect to the proximal drive sleeve 142 which is still rotationally constrained in inner body 20 as clicker parts 101 and 102 are pressed together by compressed spring 103.

As the distal drive sleeve 141 rotates, last dose nut 50 is reset to its (distal) start position. Coupling the cartridge holder 11 to inner body 20 backs off the mechanism due to the bayonet structure allowing re-engagement of the proximal drive sleeve 142 with coupler 143 and thus the distal drive sleeve 141.

A zero unit rotational hard stop 164 is provided at a distal end of the display member 160, in particular at the distal end of its number sleeve 161. This stop 164 axially and/or circumferentially abuts with a stop 24 formed on the outer circumference of the inner body 20. Correspondingly and in proximal direction 5 the thread 21 is terminated by a proximal stop 25 that may engage with the inner thread 163 or a stop feature provided on the inside of the number sleeve 161. A proximal or maximum dose stop may be also located on an inside of the proximal housing 12 to engage with an axially extending stop feature 167 at a proximal end of the number sleeve 161.

Figure 14:
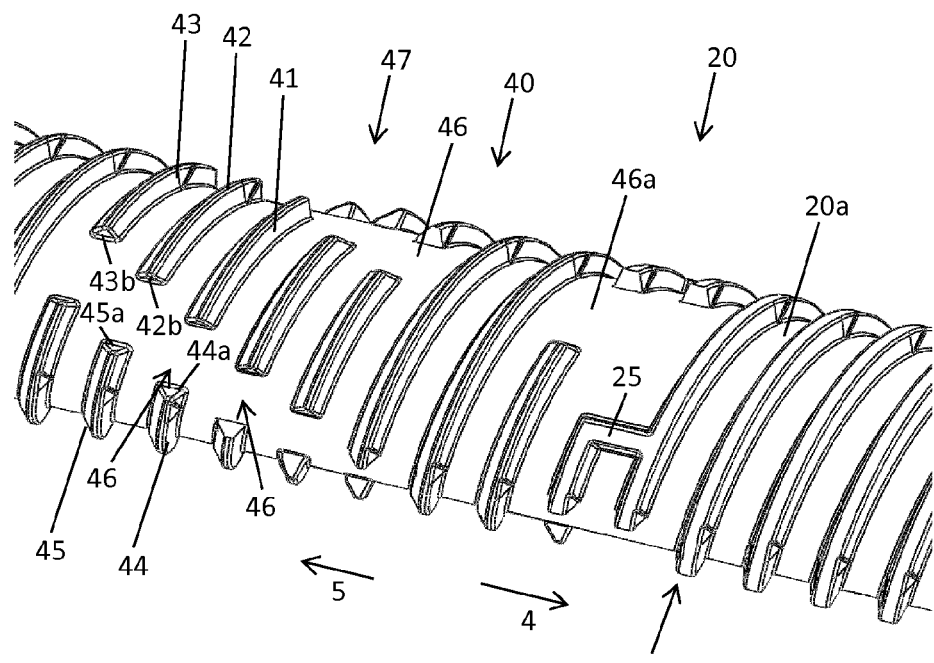
FIG. 14 is a perspective illustration of part of the inner body.
Figure 15:
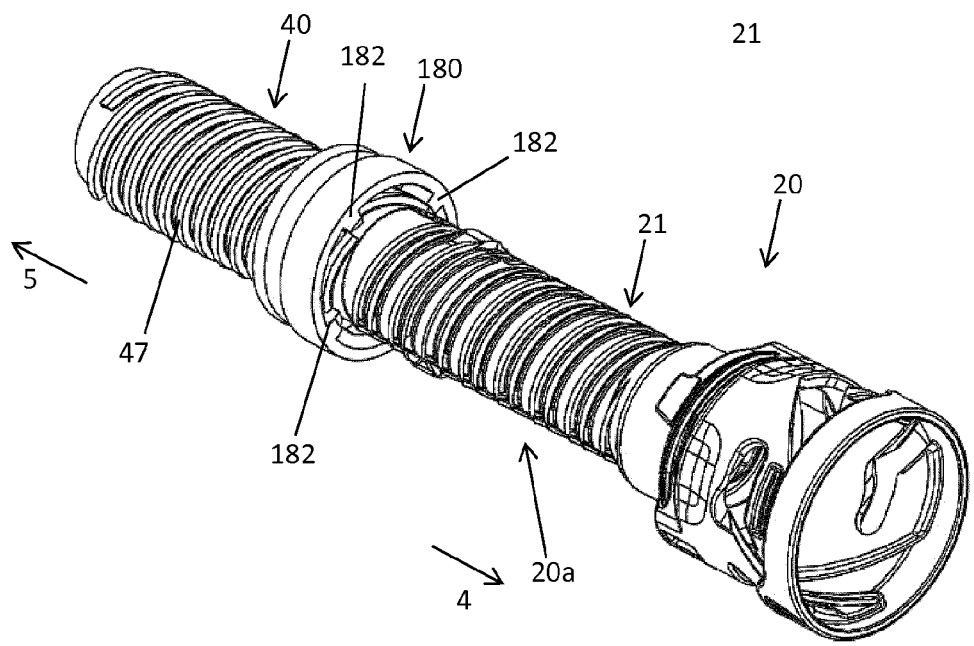
FIG. 15 is a perspective illustration of the inner body with the blocking ring attached thereto.

As it is apparent from FIGS. 14 and 15, the inner body 20 comprises an elongated shaft 20a. Along the outer circumference of the elongated shaft 20a there is provided an outer thread 21 by way of which the inner body 20 is threadedly engaged with a radially inwardly extending thread feature or inner thread 163 of the display member 160 as shown in the cross-section in FIG. 17. In the present embodiment the outer thread 21 is located in a distal portion of the inner body 20. The elongated shaft 20a and hence the inner body 20 further comprises a blocking structure 40. In the present embodiment the blocking structure 40 is located at a proximal portion of the elongated shaft 20a. It is also located on the outer circumference of the elongated tubular shaft 20a. As shown in FIGS. 14 and 15, the outer thread 21 and the blocking structure 40 are axially separated. Hence, the outer thread 21 and the blocking structure 40 are axially non-overlapping.

The blocking structure 40 comprises or forms at least one blocking thread 47. The blocking thread 47 and the outer thread 21 have the same pitch and are of the same lead. It is in principle also possible that the axial positions of outer thread 21 and blocking structure 40 interchange so that the outer thread 21 is located at a proximal end of the elongated shaft 20a and that the blocking structure 40 is located at a distal end of the shaft 20a. Moreover the blocking structure 40 and the outer thread 21 could also be arranged at least partially overlapping in the axial direction. Hence, the blocking structure 40 or the blocking thread 47 may be located axially in between successive convolutions of the outer thread 21 and vice versa.

Figure 12:
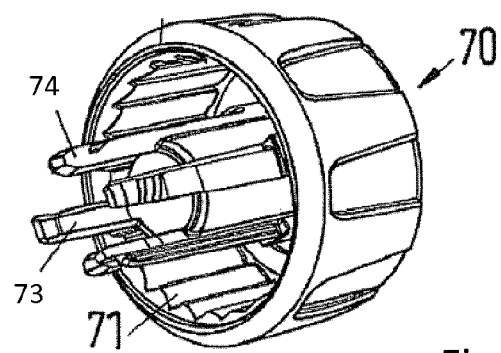
FIG. 12 shows a proximal part of the dose member.
Figure 13:
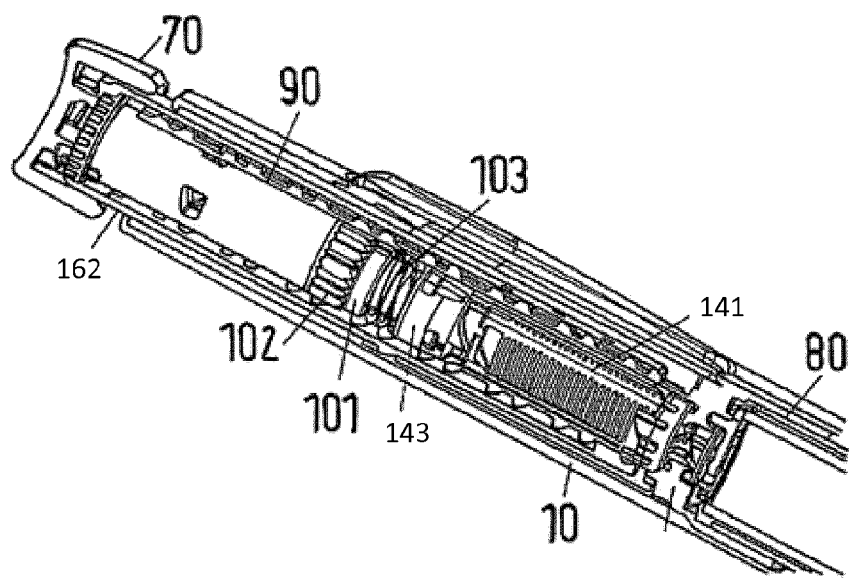
FIG. 13 is a partially cut view through the drive mechanism when assembled in the injection device.

The display member 160 and in particular the dial sleeve 162 thereof comprises a radially inwardly directed stepped down portion at its proximal end and is hence selectively rotationally engageable with the clutch sleeve 90, which in turn is axially fixed to the dose member 70. Via said clutch sleeve 90 and the mutually engaging teeth 95 or clutch features 165 the dose member 70 is selectively rotationally engageable with the dial sleeve 162 and hence with the display member 160. In this way a clutch C between the dose member 70 and the display member 160 is provided. As shown in FIG. 12 the dose member 70 comprises a dose button 71 with arms 73 and snap features 74 by way of which it is axially and rotationally locked to the clutch sleeve 90.

There is further provided a blocking ring 180 that is at least selectively axially engageable with the dose sleeve 172 and hence with the dose member 70. As shown in FIG. 17 the dose member 70 comprises a dose button 71 or dose dial that is axially fixed to a dose sleeve 172. The dose sleeve 172 extends in the axial direction and is located outside the display member 160 and hence outside the dial sleeve 162. The dial sleeve 162 and the number sleeve 161 of the display member 160 are rigidly attached and mutually fastened. The dose sleeve 172 surrounds at least a portion of the dial sleeve 162 and is displaceable in the axial direction relative to the display member 160, hence also relative to the number sleeve 161 and to the dial sleeve 162 at least by a predefined axial distance.

The blocking ring 180 is rotationally fixed to the display member 160. It comprises at least one blocking element 182 to axially engage with the blocking structure 40 and for blocking an axial displacement of the dose sleeve 172 and the dose member 70 from the dose setting position S towards a dose dispensing position D. The blocking ring 180 encloses at least a portion of the display member 160. Furthermore it is axially displaceable relative to the display member 160 at least by a predefined axial distance. This axial distance is at least as large as the distance which is required to disengage the clutch C between the display member 160 and the dose member 70 or the clutch sleeve 90.

Figure 19:
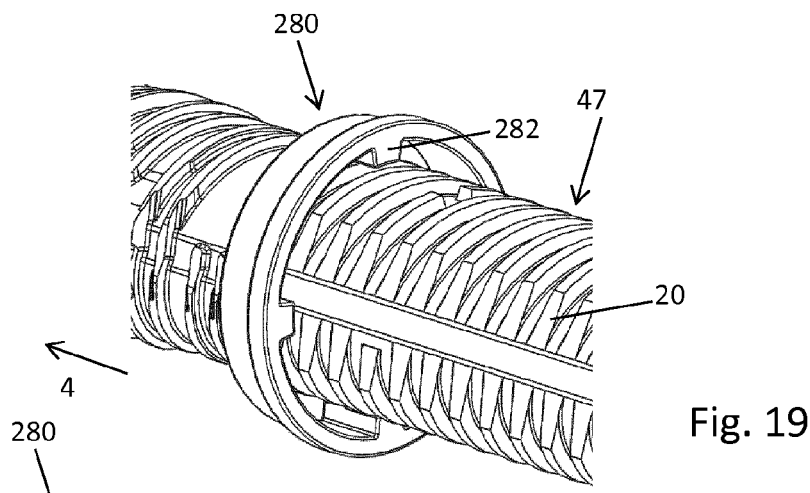
FIG. 19 is a perspective and enlarged illustration of the inner body with the blocking ring.
Figure 20:
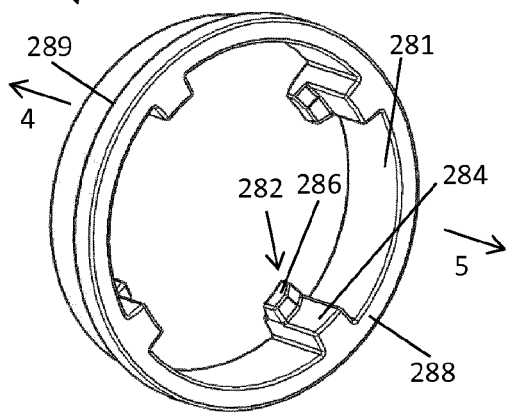
FIG. 20 is an enlarged view of the blocking ring.
Figure 21:
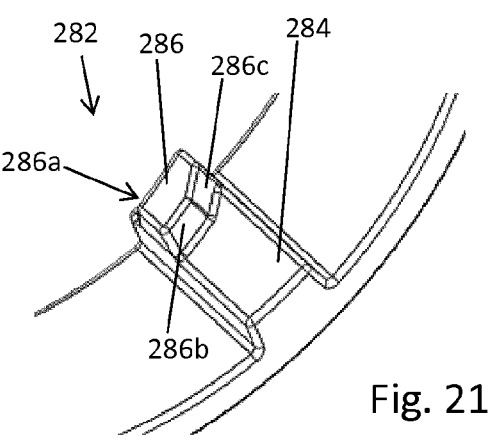
FIG. 21 shows an enlarged section of FIG. 20.

As shown in greater detail in FIGS. 19-21 the blocking ring 180 comprises several, e.g. four radially inwardly protruding blocking elements 182. The blocking elements 182 are rigidly fastened to or integral with the inside of the blocking ring 180. In the illustrated embodiment the four blocking elements 182 are equidistantly arranged in circumferential direction and are located in a common lateral plane perpendicular to the longitudinal extension of the elongated shaft 20a or of the elongated display member 160. The display member 160 comprises numerous through openings or apertures 193 in its tubular-shaped sidewall 191, 192. The apertures 193 are configured as longitudinal slits through which the blocking elements 182 of the blocking ring 180 extend radially inwardly. Furthermore the blocking elements 182 are allowed to slide in the axial direction inside the apertures 193. The tangential or circumferential width of the apertures 193 closely matches with the tangential width w or tangential size of the various blocking elements 182. Since the blocking elements 182 extend radially inwardly through the apertures 193 there is formed a permanent rotational interlock between the blocking ring 180 and the display member 160.

One embodiment of the blocking structure 40 is shown in more detail in FIG. 14. The blocking thread 47 is interrupted or intersected by various gaps 46 extending between numerous blocking segments of which only blocking segments 41, 42, 43, 44 and 45 are denoted with reference numbers. The blocking segments 41, 42, 43, 44, 45 belong to the blocking thread 47 and constitute or form the intersected blocking thread 47. The blocking segments 42, 45 are aligned in tangential direction in accordance to the pitch of the blocking thread 47. Tangentially between a tangential end 42b of the blocking segment 42 and a tangential end 45a of the consecutive or neighboring blocking segment 45 there is provided a gap 46 having a predefined tangential or circumferential size. The tangential gap size 46 is at least as large as the tangential width w of the radially inwardly extending blocking elements 174.

Likewise the blocking segments 42, 45 two further blocking segments 41, 44 that are also separated at their tangential ends 41b, 44a by a gap 46 are located axially offset from the blocking segments 42, 45. The gaps 46 between the blocking segments 42 and 45 and between the blocking segments 41 and 44 are somewhat tangentially or circumferentially offset. The axial as well as circumferential position and size of the gaps 46 define discrete dose sizes or a range of a minimum and a maximum dose that can be set and dispensed by the drive mechanism 2. In an initial or zero dose configuration the blocking elements 174 of the blocking sleeve 172 are located near a distal end of the blocking thread 47.

Near a distal end of the blocking structure 40 there is provided an initial gap 46a. At the end of a dose dispensing procedure the protrusions 186 of the at least one blocking element 182 will be co-aligned with this initial gap 46a so as to allow and to support a proximally directed returning of the blocking ring 180 and dose member 70 towards its dose setting position S.

As a dose is dialed the blocking ring 180 rotates in unison with the display member 160. Consequently and according to the specific geometric design of the blocking structure 40 the blocking elements 182 are located axially offset from the various blocking segments 41, 42, 43, 44, 45 of the blocking structure 40. When dialing a dose radially inwardly directed protrusions 186 of the blocking elements 182 are located axially between two axially consecutive convolutions of the blocking thread 47. In typical embodiments a distally facing beveled edge of the blocking elements is located in close proximity to the proximal edge 49 of the blocking thread 47. They may even come into a contact arrangement with the blocking thread. Due to the identical pitch of the outer thread 21 and the blocking thread 47 and due to the coupling between the display member 160 and the dose member 70 via the clutch sleeve 90 the blocking elements 182 remain in a constant proximal position relative to the blocking thread 47 as the dose member 70 or the dose sleeve 172 is subject to a dose dialing rotation.

At the end of a dose setting or dose dialing procedure the blocking elements 182 may either be located in a position at least partially tangentially overlapping with a distally located blocking segment 41, 42, 43, 44 or 45 or the blocking elements 182 align with or may be located with their complete tangential size inside the at least one gap 46. In the latter case the dose member 70 and the blocking elements 182 of the blocking ring 180 are in a release position R. As the blocking elements 182 are axially aligned with respective gaps 46 of the blocking structure 40 the blocking structure 40 actually allows and supports a distally directed axial displacement of the blocking elements 182 relative to the blocking structure 40.

Due to the distally directed axial displacement of the blocking ring 180 the clutch C is allowed to disengage, thereby switching the drive mechanism 2 into the dose dispensing mode D. During dose dispensing a user applies distally directed pressure or thrust to the dose button 71. Under this force and due to the mutual interaction of dose member 70, driver 140, inner body 20 and the display member 160 the display member starts 160 to rotate in a dose decrementing direction so that dose size indicators, such as numbers printed on the outer circumference of the number sleeve 161 appear in a decreasing order in the window 14 of the proximal housing part 12. In the event that dose dispensing is interrupted the spring 103 tends to displace the clutch sleeve 90 and the dose member 70 back into the proximal end position.

Since the at least one blocking element 182 is subject to a rotation relative to the inner body 20 during the dose dispensing procedure its protrusions 186 may re-enter the blocking thread 47. Such a re-entry is always possible as long as the dose member 70 and the blocking ring 180 remain in the distal dose dispensing position D. Then, the respective protrusion 186 is allowed to enter a distally neighboring convolution of the blocking thread 47 so that the protrusion 186 is located distally from a distal edge of said convolution.

In other configurations where a user selects or dials a dose that is not intended to be dispensed by the injection device 1 there will be at least a partial tangential and radial overlap of the protrusions 186 with one of the blocking segments 41, 42, 43, 44, 45 as seen in the axial direction.

In such configurations, if a user depresses the dose member 70 by pressing on the dose button 71 in distal direction 4 the axial engagement and the axial abutment of the protrusion 186 of the blocking element 182 with the blocking thread 47 or with one of its blocking segments 41, 42, 43, 44, 45 blocks and prevents a distally directed displacement of the blocking ring 180. Since the dose member 70 with its dose sleeve 172 is in axial abutment with the blocking ring 180 the dose member 70 cannot be depressed in distal direction 4. Hence, the clutch C cannot disengage and dispensing of the dose cannot take place.

Figure 16:
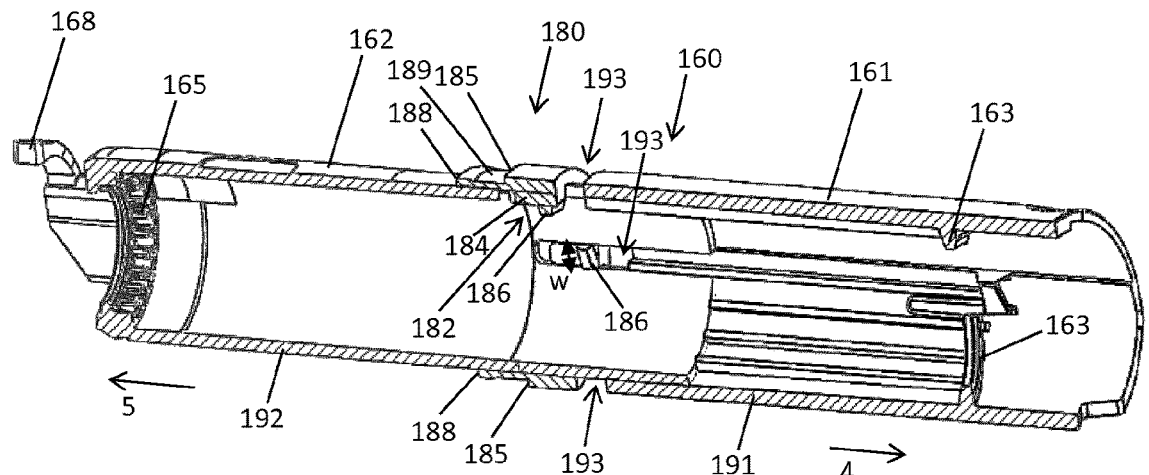
FIG. 16 shows a longitudinal cross-section of a first embodiment of the blocking ring engaged with the display member.
Figure 27:
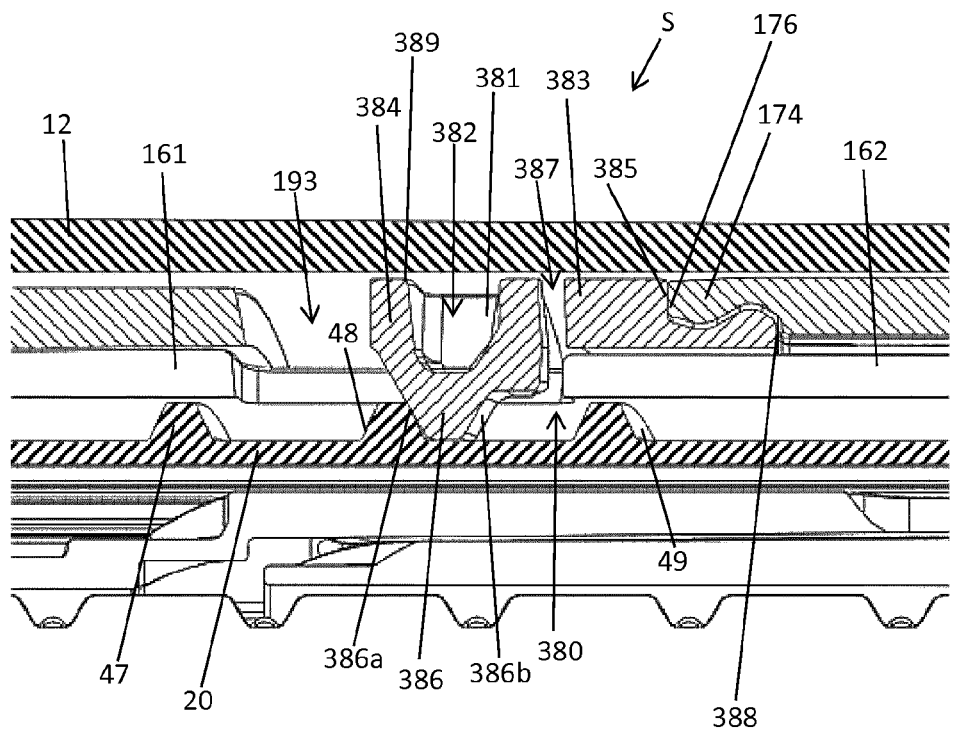
FIG. 27 is a longitudinal cross-section of the embodiment according to FIG. 26, FIG. 28 corresponds to FIG. 27 but with the blocking ring in blocking engagement with the blocking structure

In the embodiments as shown in FIGS. 16, 17 and FIGS. 26-29 the blocking ring 180, 380 is permanently axially connected to the dose member 70. As it is shown in FIGS. 16, 17 and 27 the blocking ring 180, 380 and the dose sleeve 172 are axially fastened but the blocking ring 180,380 may rotate relative to the dose sleeve 172. This rotational decoupling is beneficial during dose dispensing where the display member 160 and hence the blocking ring 180, 380 rotates while the dose sleeve 172 is subject to a non-rotating axial displacement relative to the housing 10.

The blocking ring 180 comprises a stepped down section 185 as shown in FIG. 16 that faces in proximal direction 5. When engaged with the dose sleeve 172 a distal end face 176 of the dose sleeve 172 axially abuts with the stepped down section 185. Moreover at the proximal end of the reduced diameter of the blocking ring 180 there is provided a further end face 188 that may axially abut with a correspondingly-shaped distally facing abutment face of the dose sleeve 172. The dose sleeve 172 comprises a fastening element 174 at its distal end section to engage with a corresponding fastening structure 189 at the proximal end of the blocking ring 180. The fastening structure 189 comprises a radially recessed annular section near the stepped down section 185 and it may further comprise a radially thickened annular structure, e.g. having a beveled edge in order to provide a kind of a snap fit engagement with the dose sleeve 172. In FIG. 27 the mutual interconnection of the dose sleeve 172 with the blocking ring 380 is shown in greater detail. There, the stepped down section 385 is in axial abutment with the distal end face 176 and the fastening element 174 is in snap-fit engagement with a ring portion 383 of the blocking ring 380 featuring a beveled edge at a proximal end face 388.

The rotational decoupling of the blocking ring 180 and the dose sleeve 172 is of particular benefit during dose dispensing since a proximal portion 173 of the dose sleeve 172 extends beyond the proximal end of the housing 12 after a dose has been set. Having the dose sleeve 172 rotationally decoupled from the blocking ring 180 and hence from the rotating display member the dose sleeve 172 is not subject to a rotation during dose dispensing so that a user cannot accidentally stall the dispensing procedure.

As it is further apparent from FIG. 16 the blocking element 182 comprises an axially elongated base portion 184 that extends radially inwardly from the sidewall 181 of the blocking ring 180. At a distal end of the base portion 184 a toothed or cam-shaped protrusion 186 extends further inwardly in radial direction. When in blocking engagement with the blocking structure 40 it is only this protrusion 186 that axially engages with the blocking structure 40 while the base portion 184 remains radially outside the blocking thread 47. The rather small and thin protrusion 186 can be mechanically stabilized by the base portion 186 with regard to deflection or deformation. The base portion 186 may act as a kind of support feature to improve mechanical load transfer through the blocking element 182 and to provide an improved mechanical stability of the blocking element 182.

In this way the blocking elements 182 comprise a rather rigid and solid structure. This is of particular benefit also for device assembly, where the radially inwardly protruding blocking elements 182 have to slide over the outer circumference of the display member 160 until they snap into the apertures 193. In the present embodiments the display member 160 comprises two components, namely a number sleeve 161 and a dial sleeve 162. The aperture 193 may be provided in the sidewall 191 of the number sleeve 161 and/or in the sidewall 192 of the dial sleeve 162.

In the embodiment of FIGS. 18-25 a different kind of dose member 270 and a different kind of a blocking ring 280 is provided. There and in contrast to the embodiment of FIGS. 16 and 17 the blocking ring 180 does not have of an axial connection with the dose member 270. As shown in greater detail in FIG. 22 the dose member 270 comprises a planar-shaped dose button 271 that is coupled and fixed to a dial portion 273 of an axially elongated and tubular-shaped dose sleeve 272. The dose sleeve 272 comprises a distal end face 276 that axially abuts with a correspondingly-shaped end face 288 of the blocking ring 280. These faces form an axial abutment between the dose sleeve 272 and the blocking ring 280. In this way the blocking ring 280 is only displaceable in distal direction 4 by means of the dose sleeve 272 and hence by the dose member 270.

Figure 22:
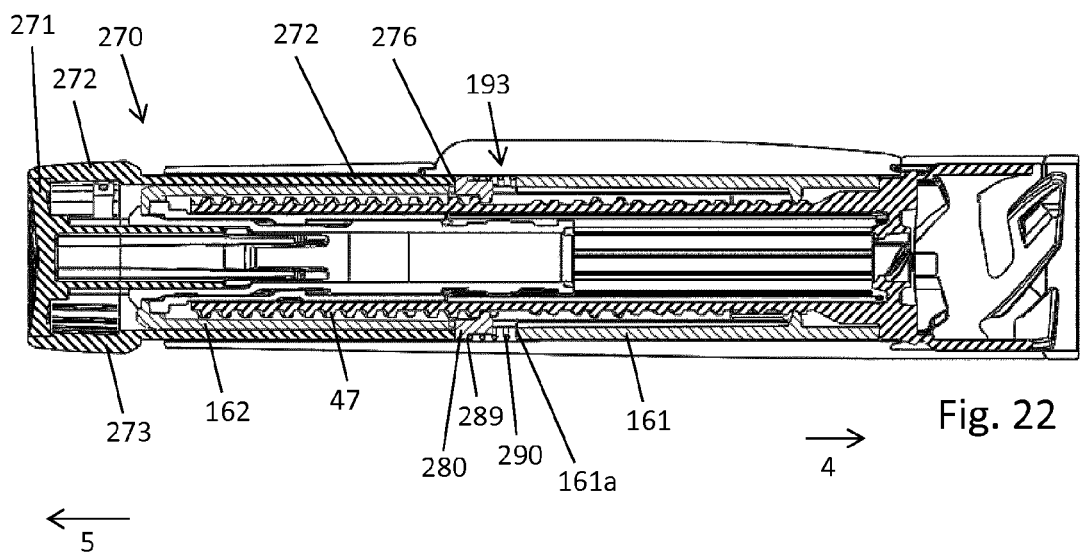
FIG. 22 is a longitudinal cross-section through the drive mechanism according to FIG. 18.

For returning of the blocking ring 280 to its initial proximal position a spring element 290 is provided, as illustrated in FIG. 22. By means of the spring element 290 the blocking ring 280 is biased against the number sleeve 161 in proximal direction 5. In this way the blocking ring 280 is kept in axial abutment with the distal end of the dose sleeve 272. For this the blocking ring 280 comprises a radially outwardly extending flange portion 289 at its proximal end. As shown in FIG. 22, the proximal end of the spring element 290 is in axial engagement with this flange portion 289. The opposite end of the spring element 290 is in axial engagement either with a correspondingly-shaped flange portion or with a proximally facing end face 161a of the number sleeve 161. From a constructional point of view it may be beneficial when the blocking ring 280 and the spring element 290 are located in an interface section between the number sleeve 161 and the dial sleeve 162. The number sleeve 161 and the dial sleeve 162 may still be rigidly fastened to each other, e.g. by means of a snap fit engagement or the like.

Figure 23:
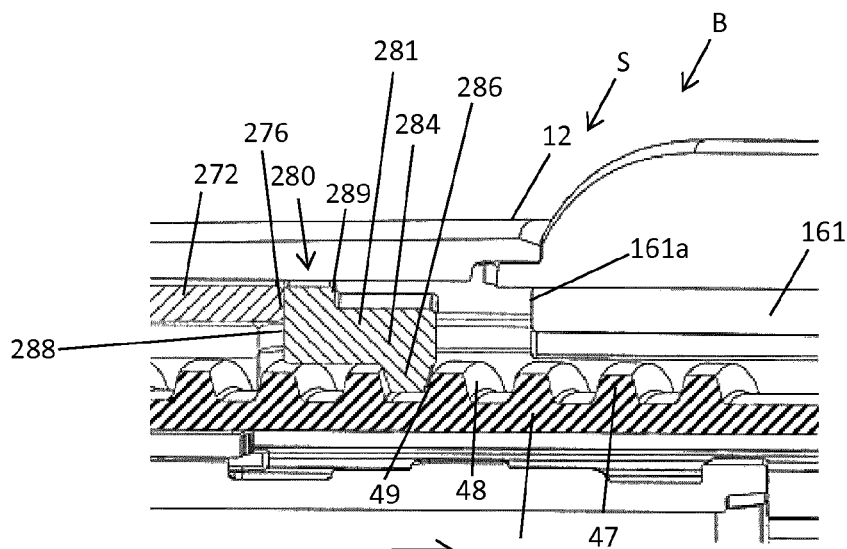
FIG. 23 is an enlarged view of the engagement of the blocking ring and the blocking structure in accordance to FIGS. 18 and 22 in a blocking configuration, FIG. 24 corresponds to the illustration of FIG. 23 but in a release configuration, FIG. 25 corresponds to FIG. 24 but with the blocking element trapped in a distal position as a dispensing action is interrupted or paused.
Figure 24:
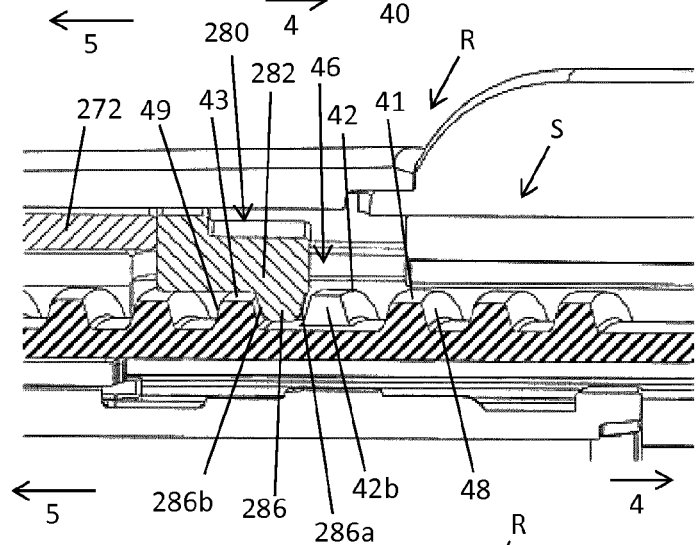
Figure 25:
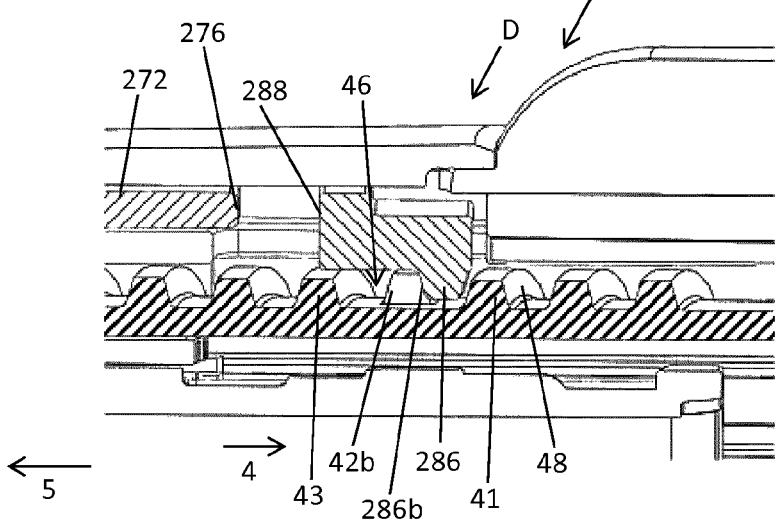
Figure 26:
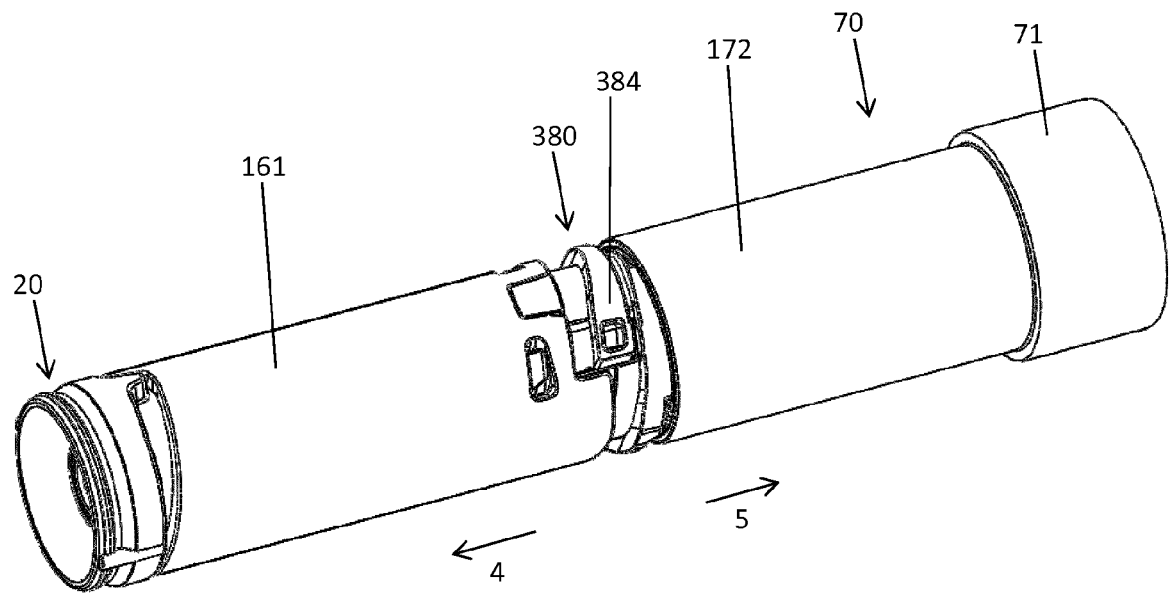
FIG. 26 shows a further embodiment of the blocking ring with at least one curved cantilever portion.

The blocking functionality of the blocking ring 280 is somewhat identical to the one described above in connection with the blocking ring 180. In FIGS. 23-25 the interaction between the blocking ring 280 and the blocking structure 40 is shown in greater detail. The blocking ring 280 comprises four blocking elements 282 extending radially inwardly from the annular sidewall 281 of the blocking ring 280. Each blocking element 282 comprises a base portion 284 extending all along the axial extension of the blocking ring 280. At a distal end the blocking elements 282 comprise a protrusion 286 extending from the base portion 284 further inwardly. As shown in FIGS. 23-25 it is only the protrusion 286 that enters the free space between axially neighboring convolutions or blocking segments 41, 42, 43, 44, 45 of the blocking thread 47. In FIG. 23 a configuration is shown, where the protrusion 286 is located between two axially neighboring convolutions of the blocking thread 47. In this blocking configuration B the blocking ring 280 is hindered from a distally directed displacement. Since the dose member 270 is in axial abutment with the blocking ring 280 a distally directed depression of the dose member 270 is blocked and impeded. Assuming that a distally directed pressure would be applied to the dose member 270 a distally facing end face or distal edge 286a would abut with a proximal edge 49 of the blocking thread 47 of the blocking structure 40.

When a dose is dialed that is allowed to be dispensed the protrusion 286 will align and overlap with a gap 46 in the blocking structure 40. Such a configuration is shown in FIG. 24. It is then allowable and possible for the blocking ring 280 to pass adjacent to a tangential end 42b of a blocking segment 42. The dose member 270 and dose sleeve 272 are displaceable in distal direction 4 together with the blocking ring 280 relative to the inner body 20 and hence relative to the display member 160. Dose dispensing may therefore start. During dose dispensing the display member 160 is subject to a dose decrementing rotation relative to the inner body 20. Consequently, the protrusion 286 will re-engage with the blocking structure 40. During dispense the blocking ring 280 will be kept by the engagement with the blocking structure 40 in the distal release configuration R while the dose member 270 and its dose sleeve 272 may be subject to a proximally directed returning, e.g. when dose dispensing should be interrupted or paused.

Then and as shown in FIG. 25 a proximally facing proximal edge 286b of the protrusion 286 engages with the blocking thread 47 and axially buts with a distally facing distal edge 48 of the blocking thread 47. The axial detachment between the blocking ring 280 and the dose member 270 allows for a complete returning of the dose member 270 into its initial dose setting position S if a dose dispensing procedure should be interrupted or paused. Consequently the clutch C will re-engage and dose dialing or correction of a dose will be possible even before the initially set dose has been completely dispensed. If dose dispensing is interrupted it may be immediately resumed since the blocking ring 280 is kept in the distal release position.

In FIG. 21 it is further illustrated that the protrusions 286 also comprise a ramped face 286c tangentially adjacent to the proximal edge 286b. This ramped face 286c provides a rather smooth engagement with the blocking structure 40 during dose dispensing. In such situations where a distally directed displacement of the blocking elements 282 is not far enough to fully clear the distal face or distal edge 48 of the blocking thread 47 the blocking ring 280 will be pulled distally by the action of the ramped faces 286c against a distal side or distal edge 48 of the blocking thread 47. This ensures that the blocking elements 282 run along the blocking thread 47 smoothly and correctly even if the thread is locally cut away to aid moulding, as shown in FIG. 19. The spring element 290 is omitted in FIGS. 23-25 to simplify the illustrations.

In FIGS. 26-29 a further embodiment of the blocking ring 380 is shown. There and in contrast to the other embodiments the blocking ring 380 comprises an annular ring portion 382 and at least one curved cantilever portion 384 permanently attached to the ring portion 383. The curved cantilever portion 384 forms a flexible arm that extends around part of the circumference of the ring portion 383. It is located axially offset to the ring portion 383. As shown in FIG. 27 the curved cantilever portion 384 is located distally from the ring portion 383. The ring portion 383 is permanently axially engaged with the dose sleeve 172. The positive engagement by means of mutually corresponding annular-shaped snap features provide a bi-directional axial engagement between the blocking ring 380 and the dose sleeve 172 while allowing rotation of the blocking ring 380 relative to the dose sleeve 172.

The curved cantilever portion 384 comprises a protrusion 386 extending radially inwardly from a sidewall 381 of the curved cantilever portion 384. The protrusion 386 actually forms a blocking element 382 to axially engage with the blocking structure 40 on the outer circumference of the inner body 20. So the basic functionality of the blocking element 382 is similar to the blocking element 182 as described above. The blocking element 382 extends radially inwardly through the aperture 193 in the sidewall 191 of the number sleeve 161 or in the sidewall 192 of the dial sleeve 162. The blocking ring 380 is rotationally locked to the display member 160 in the same way as described above and by means of the radially inwardly protruding blocking element 382.

The curved cantilever portion 384 is flexible. It exhibits a particular flexibility in the radial direction. Moreover, on its radially outwardly facing surface it comprises a brake surface 389 to frictionally engage with an inner sidewall section of the housing part 12. The curved cantilever portion 384 is rather stiff in axial direction. At least its flexibility in radial direction is much larger than in axial direction. Similar to the configuration described with the blocking ring 280 in connection with FIGS. 23-25 the protrusion 386 comprises a distal edge 386a as well as a proximal edge 386b. These edges 386a, 386b are beveled and communicate or correspond to the beveled distal and proximal edges 48, 49 of the blocking thread 47.

When the curved cantilever portion 384 and the blocking element 382 come into axial abutment with the blocking thread 47 and if the blocking ring 380 experiences a small distally directed displacement 4 the curved cantilever portion 384 is immediately urged radially outwardly so that the brake surface 389 immediately contacts and frictionally engages with the inside facing sidewall portion of the housing part 12. This is shown in greater detail in FIG. 28. A rotational braking effect is even achieved before the ring portion 383 axially abuts with the curved cantilever portion 384. As it is apparent from a comparison of FIGS. 27 and 28 when in a blocking configuration B an initial gap 387 allowing for an unhindered radial deflection and pivoting of the curved cantilever portion 384 will be closed. In the blocking configuration B a major part of the mechanical load applied to the dose member 70 will be transferred through the axial abutment between the protrusion 386 and the blocking thread 47.

Figure 28:
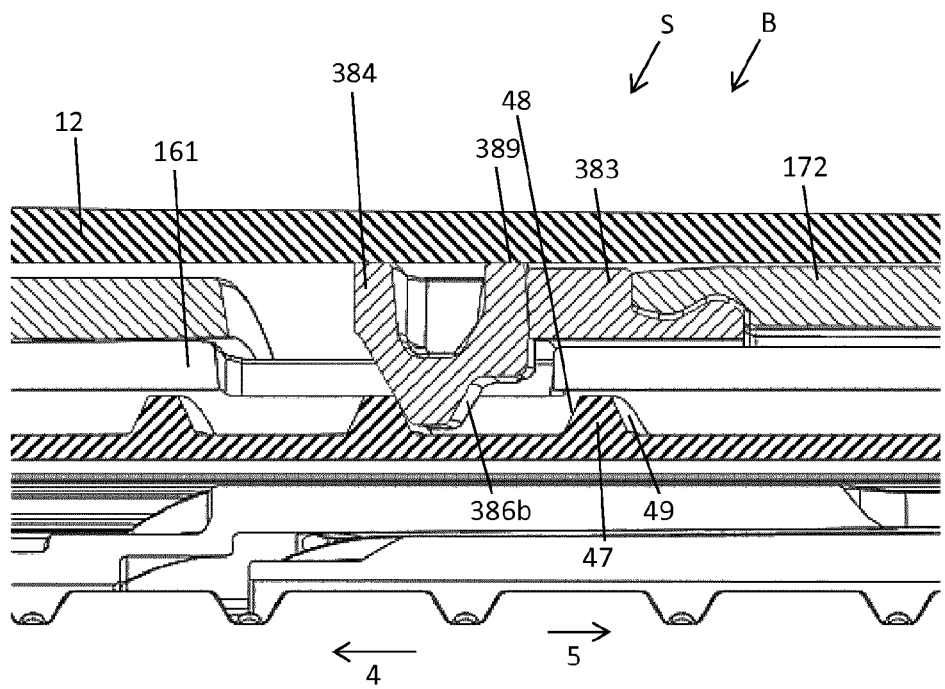
Figure 29:
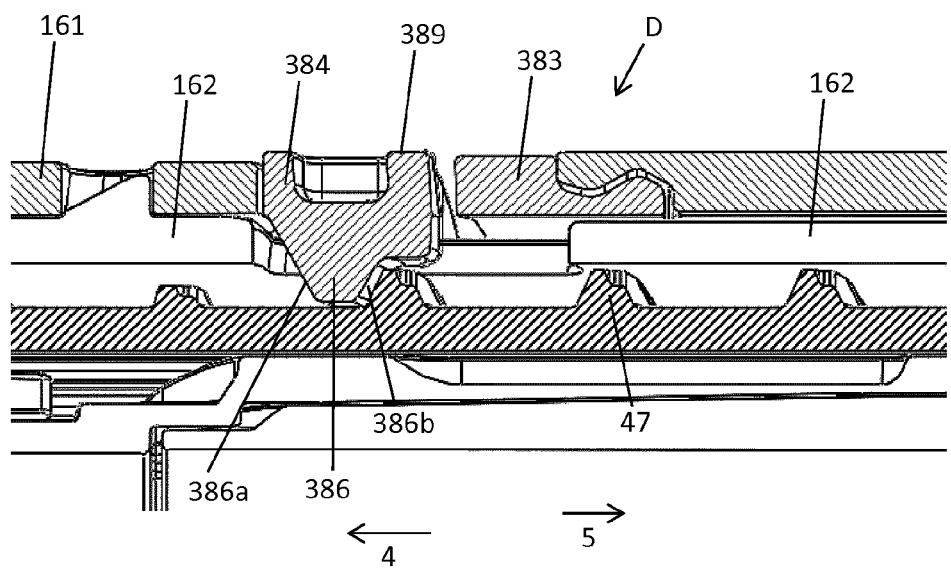
FIG. 29 shows the blocking ring in a dose dispensing position.

The embodiment according to FIGS. 27-29 is of particular benefit when for instance one unit or one discrete dose size should be dialed above or below an unblocked position. In such a configuration the blocking mechanism as described in connection with FIGS. 1 to 25 may be subject to slip and may inadvertently disengage as the dose member 70 is depressed in distal direction. This is because the display member 160 will be subject to a slight rotation with regard to the outer thread 21 of the inner body 20 as a user presses the dose member 70 to attempt to dispense a dose. As the display member 160 carries with it the blocking ring 180, 280 the blocking engagement between the blocking elements 182, 282 with the blocking thread 47 will reduce. As a result of geometric tolerances of the components of the drive mechanism and necessary running clearances it may happen that the mutual engagement between the blocking elements 181, 281 and the blocking structure 40 becomes insufficient to prevent the blocking elements 182, 282 and the blocking structure 40 from deforming, slipping or disengaging. With the at least one radially outwardly deflecting curved cantilever portion 384 such a small initial rotation of the display member 160 and hence of the blocking ring 380 can be effectively prevented.

It is even conceivable, that the curved cantilever portion 384 is slightly biased in distal direction 4 so that it smoothly slides along the proximal edge 49 of the blocking thread 47 so as to guarantee that there is a permanent contact between the proximal edge 49 and the distal edge 386a. Apart from that the blocking ring 380 behaves in the same way as the blocking ring 180 described above.

In addition, the flexibility of the curved cantilever portion 384 is of particular benefit when for instance a dose dispensing procedure is interrupted or paused. Such a configuration is shown in FIG. 29 which is somewhat equivalent to the configuration as shown in FIG. 25. There, the proximal edge 386b is located on a distal side and hence distally from the distal edge 48 of the blocking thread 47. Since the blocking ring 380 and in particular its ring portion 383 is permanently axially fixed to the dose sleeve 172 and hence to the dose member 270 a pulling on the dose member 270 in proximal direction will lead to a rather strong deflection of the curved cantilever portion 384 relative to the rather solid and rigid ring portion 383. But here and in contrast to the embodiment of FIGS. 16 and 17 the flexible behavior of the curved cantilever portion 384 acts as a kind of suspension so that forces applied to the dose member 270 cause a deflection of the curved cantilever portion 384 rather than disengagement of ring portion 383 from the dose sleeve 172.

LIST OF REFERENCE NUMBERS 1 injection device
2 drive mechanism
4 distal direction
5 proximal direction
10 housing
11 cartridge holder
12 outer body
13 layer
14 window
15 aperture
216 thread
20 inner body
20a shaft 21 outer thread
22 spline
23 inner thread
24 stop
25 stop
30 piston rod
31 outer thread
32 outer thread
33 bearing
40 blocking structure
41 blocking segment
42 blocking segment
42b tangential end
43 blocking segment
43b tangential end
44 blocking segment
44a tangential end
45 blocking segment
45a tangential end
46 gap
46a gap
47 blocking thread
48 distal edge
49 proximal edge
50 last dose nut
51 external rib
52 inner thread
53 stop
70 dose member
71 dose dial/dose button
73 arm
74 snap feature
80 cartridge
81 reservoir
82 bung
83 crimped metal cap
90 clutch sleeve
91 splines
92 teeth
93 aperture
94 splines
95 teeth
100 clicker
101 distal clicker
102 proximal clicker
103 clutch spring
104 splines
105 clicker teeth
106 clicker teeth
107 splines
108 splines
109 teeth
110 cartridge bias spring
120 cap
140 driver
141 distal drive sleeve
142 proximal drive sleeve
142 inner thread
143 coupler
144 thread
145 stop
146 teeth
147 teeth
148 flexible finger
149 hook
160 display member
161 number sleeve
161a end face
162 dial sleeve
163 inner thread
164 stop
165 clutch feature
166 bearing face
167 stop
168 clicker
172 dose sleeve
173 proximal end
174 fastening element
176 end face
180 blocking ring
181 sidewall
182 blocking element
184 base portion
185 stepped section
186 protrusion
188 end face
189 fastening structure
191 sidewall
192 sidewall
193 aperture
270 dose member
271 dose button
272 dose sleeve
273 dial portion
276 end face
280 blocking ring
281 sidewall
282 blocking element
284 base portion
286 protrusion
286a distal edge
286b proximal edge
286c ramped face
288 end face
289 flange portion
290 spring element
380 blocking ring
381 sidewall
382 blocking element
383 ring portion
384 curved cantilever portion
385 stepped section
386 protrusion
386a distal edge
386b proximal edge
388 end face
387 gap
389 brake surface

The invention claimed is:

1. A drive mechanism for an injection device for setting and dispensing of a dose of a medicament, the drive mechanism comprising:
an inner body fixable inside a housing of the injection device, the inner body comprising an elongated shaft extending in an axial direction, wherein the elongated shaft comprises an outer thread and a blocking structure on an outer circumference of the elongated shaft;
a tube-shaped display member having an inner thread engaged with the outer thread of the inner body;
a dose member axially displaceable relative to at least one of the inner body or the display member between a dose setting position and a dose dispensing position; and
a blocking ring axially engageable with the dose member, rotationally fixed to the display member, and comprising at least one blocking element to axially engage with the blocking structure for blocking an axial displacement of the dose member from the dose setting position towards the dose dispensing position.

2. The drive mechanism of claim 1, wherein the blocking structure comprises a blocking thread axially extending on the elongated shaft of the inner body, wherein the blocking thread and the outer thread have the same pitch.

3. The drive mechanism of claim 1, wherein the blocking structure comprises at least two spiral-shaped blocking segments separated in a tangential direction by at least one gap having a tangential size larger than or equal to a tangential size of the at least one blocking element.

4. The drive mechanism of claim 1, wherein the blocking ring encloses at least a portion of the display member, and the at least one blocking element protrudes radially inwardly from a sidewall of the blocking ring.

5. The drive mechanism of claim 4, wherein the at least one blocking element extends radially inwardly through an aperture in a sidewall of the display member.

6. The drive mechanism of claim 1, wherein the dose member comprises a dose button and an elongated tubular dose sleeve, wherein the dose button is axially fixed to a proximal end of the dose sleeve.

7. The drive mechanism of claim 6, wherein the dose sleeve comprises a distal face to axially abut with a proximal face of the blocking ring.

8. The drive mechanism of claim 6, wherein the dose sleeve is axially fixed to the blocking ring.

9. The drive mechanism of claim 6, wherein the blocking ring is displaceable in a distal direction relative to the display member against the action of a spring element.

10. The drive mechanism of claim 6, wherein the blocking ring and the dose sleeve are rotationally decoupled.

11. The drive mechanism of claim 1, wherein the blocking ring comprises an annular ring portion and at least one curved cantilever portion located axially offset to the ring portion, and the at least one blocking element is located at a free end of the at least one curved cantilever portion, wherein the at least one curved cantilever portion is configured to deflect radially outwardly when its the at least one blocking element axially engages with the blocking structure.

12. The drive mechanism of claim 11, wherein the at least one curved cantilever portion is flexible and exhibits a higher degree of flexibility in a radial direction than in the axial direction.

13. The drive mechanism of claim 1, further comprising a piston rod and a tube-shaped driver extending in the axial direction, wherein the piston rod comprises a first outer thread engaged with an inner thread of the inner body and comprises a second outer thread of opposite hand engaged with an inner thread of the driver.

14. The drive mechanism of claim 13, wherein the driver is rotationally locked to the dose member, and the dose member is rotationally engageable with the display member by means of a clutch which is operable to:
rotationally engage the dose member and the display member when the dose member is in the dose setting position; and
rotationally release the dose member from the display member when the dose member is in the dose dispensing position.

15. An injection device for setting and dispensing of a dose of a medicament, the injection device comprising:
a housing;
a drive mechanism arranged inside the housing, the drive mechanism comprising:
an inner body fixable inside the housing of the injection device, the inner body comprising an elongated shaft extending in an axial direction, wherein the elongated shaft comprises an outer thread and a blocking structure on an outer circumference of the elongated shaft,
a tube-shaped display member having an inner thread engaged with the outer thread of the inner body,
a dose member axially displaceable relative to at least one of the inner body or the display member between a dose setting position and a dose dispensing position, and
a blocking ring axially engageable with the dose member, rotationally fixed to the display member and comprising at least one blocking element to axially engage with the blocking structure for blocking an axial displacement of the dose member from the dose setting position towards the dose dispensing position; and
a cartridge arranged inside the housing and filled with a liquid medicament.

16. The injection device of claim 15, wherein the blocking structure comprises a blocking thread axially extending on the elongated shaft of the inner body, wherein the blocking thread and the outer thread have the same pitch.

17. The injection device of claim 15, wherein the blocking structure comprises at least two spiral-shaped blocking segments separated in a tangential direction by at least one gap having a tangential size larger than or equal to a tangential size of the at least one blocking element.

18. The injection device of claim 15, wherein the blocking ring encloses at least a portion of the display member, and the at least one blocking element protrudes radially inwardly from a sidewall of the blocking ring.

19. The injection device of claim 18, wherein the at least one blocking element extends radially inwardly through an aperture in a sidewall of the display member.

20. The injection device of claim 15, wherein the dose member comprises a dose button and an elongated tubular dose sleeve, wherein the dose button is axially fixed to a proximal end of the dose sleeve.

\* \* \* \* \*

UNITED STATES PATENT AND TRADEMARK OFFICE
CERTIFICATE OF CORRECTION

PATENT NO. : 10,835,682 B2
APPLICATION NO. : 16/061617
DATED : November 17, 2020
INVENTOR(S) : James Alexander Senior et al.

Page 1 of 1

It is certified that error appears in the above-identified patent and that said Letters Patent is hereby corrected as shown below:

On the Title Page

In Column 1, Line 20 (approx.), above "Prior Publication Data" insert -- PCT Pub. No.: WO2017/102394 PCT Pub. Date: June 22, 2017 -- as a new entry In the Claims In Column 35, Line 41 (approx.), in Claim 11, after "when" delete "its"

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*